US009669226B2

(12) United States Patent
Fontaine et al.

(10) Patent No.: US 9,669,226 B2
(45) Date of Patent: Jun. 6, 2017

(54) METHODS AND SYSTEMS FOR REDUCING INTERFERENCE IN STIMULATION TREATMENT

(75) Inventors: Nicolas Fontaine, Bottens (CH); Steve Guex, Givrins (CH); Flavien Baumgartner, Vevey (CH)

(73) Assignee: EMPI, Inc., St. Paul, MN (US)

( * ) Notice: Subject to any disclaimer, the term of this patent is extended or adjusted under 35 U.S.C. 154(b) by 1334 days.

(21) Appl. No.: 12/876,461

(22) Filed: Sep. 7, 2010

(65) Prior Publication Data
US 2012/0059436 A1    Mar. 8, 2012

(51) Int. Cl.
*A61N 1/00*        (2006.01)
*A61N 1/37*        (2006.01)
*A61N 1/372*       (2006.01)

(52) U.S. Cl.
CPC ........... *A61N 1/37* (2013.01); *A61N 1/37288* (2013.01); *A61N 1/3702* (2013.01); *A61N 1/37252* (2013.01); *A61N 1/37264* (2013.01)

(58) Field of Classification Search
CPC ... A61N 1/00; A61N 1/02; A61N 1/04; A61N 1/05; A61N 1/06; A61N 1/08; A61N 1/18; A61N 1/32; A61N 2007/0052; A61N 2007/0078; A61N 2007/0082; A61N 1/36128; A61N 1/36135; A61N 1/36139; A61N 1/36167; A61N 1/365; A61N 1/36514; A61N 1/368; A61N 1/37; A61N 1/3702; A61N 1/371; A61N 1/3712; A61N 1/37211; A61N 1/37241; A61N 1/37252; A61N 1/37264; A61N 1/37288
See application file for complete search history.

(56) References Cited

U.S. PATENT DOCUMENTS

| | | | |
|---|---|---|---|
| 4,331,157 A | 5/1982 | Keller, Jr. et al. |
| 4,398,537 A | 8/1983 | Holmbo |
| 4,690,144 A | 9/1987 | Rise et al. |
| 4,832,033 A | 5/1989 | Maher et al. |
| 5,014,705 A | 5/1991 | Graupe et al. |
| 5,033,168 A | 7/1991 | Sbragi |
| 5,109,845 A | 5/1992 | Yuuchi et al. |
| 5,478,303 A | 12/1995 | Foley-Nolan et al. |
| 5,578,060 A | 11/1996 | Pohl et al. |

(Continued)

FOREIGN PATENT DOCUMENTS

| | | |
|---|---|---|
| EP | 0 057 561 A1 | 8/1982 |
| EP | 0 552 156 A1 | 7/1993 |

(Continued)

OTHER PUBLICATIONS

PCT/IB2011/002034, International Search Report, Dec. 28, 2011.
Extended European Search Report dated Jan. 12, 2016 in European Application No. 15002322.4.

*Primary Examiner* — Edward Moran
*Assistant Examiner* — Elizabeth K So
(74) *Attorney, Agent, or Firm* — Knobbe Martens Olson & Bear LLP

(57) ABSTRACT

Systems and methods are provided for reducing stimulation interference between two stimulation modules positioned on a user's body, which may be used in stimulation systems without a central treatment controller. Systems and methods are also provided for stimulation treatment using multiple independent stimulators wirelessly managed by a remote management device.

29 Claims, 14 Drawing Sheets

(56) References Cited

U.S. PATENT DOCUMENTS

| | | |
|---|---|---|
| 5,621,951 A | 4/1997 | Gould |
| 5,704,351 A | 1/1998 | Mortara et al. |
| 5,862,803 A | 1/1999 | Besson et al. |
| 5,891,182 A | 4/1999 | Fleming |
| 5,913,284 A | 6/1999 | Van Curen et al. |
| 5,957,854 A | 9/1999 | Besson et al. |
| RE36,690 E | 5/2000 | McGraw et al. |
| 6,091,989 A | 7/2000 | Swerdlow et al. |
| 6,141,592 A | 10/2000 | Pauly |
| 6,167,258 A | 12/2000 | Schmidt et al. |
| 6,208,894 B1 | 3/2001 | Schulman et al. |
| 6,289,238 B1 | 9/2001 | Besson et al. |
| 6,324,432 B1 | 11/2001 | Rigaux et al. |
| 6,353,763 B1 | 3/2002 | George et al. |
| 6,366,816 B1 | 4/2002 | Marchesi |
| 6,434,421 B1 | 8/2002 | Taheri |
| 6,438,413 B1 | 8/2002 | Taheri |
| 6,445,955 B1 | 9/2002 | Michelson et al. |
| 6,449,511 B1 | 9/2002 | Mintchev et al. |
| 6,472,991 B1 | 10/2002 | Schulman et al. |
| 6,480,740 B2 | 11/2002 | Stahmann et al. |
| 6,493,586 B1 | 12/2002 | Stahmann et al. |
| 6,507,755 B1 | 1/2003 | Gozani et al. |
| D475,322 S | 6/2003 | Ouellette et al. |
| 6,577,893 B1 | 6/2003 | Besson et al. |
| 6,584,358 B2 | 6/2003 | Carter et al. |
| 6,587,728 B2 | 7/2003 | Fang et al. |
| 6,606,519 B2 | 8/2003 | Powell |
| 6,609,031 B1 | 8/2003 | Law et al. |
| 6,662,051 B1 | 12/2003 | Eraker et al. |
| 6,666,821 B2 | 12/2003 | Keimel |
| 6,694,180 B1 | 2/2004 | Boesen |
| 6,701,189 B2 | 3/2004 | Fang et al. |
| 6,701,190 B2 | 3/2004 | Gliner |
| 6,711,442 B1 | 3/2004 | Swerdlow et al. |
| 6,749,566 B2 | 6/2004 | Russ |
| 6,760,627 B2 | 7/2004 | Carter et al. |
| 6,792,315 B2 | 9/2004 | Carter et al. |
| 6,801,137 B2 | 10/2004 | Eggers |
| 6,811,534 B2 | 11/2004 | Bowman, IV et al. |
| 6,853,863 B2 | 2/2005 | Carter et al. |
| 6,860,896 B2 | 3/2005 | Leber et al. |
| 6,878,643 B2 | 4/2005 | Krulevitch et al. |
| 6,897,788 B2 | 5/2005 | Khair et al. |
| 6,922,589 B2 | 7/2005 | Stahmann et al. |
| 6,930,590 B2 | 8/2005 | Ling et al. |
| 6,940,403 B2 | 9/2005 | Kail, IV |
| 6,944,503 B2 | 9/2005 | Crowe et al. |
| 6,978,181 B1 | 12/2005 | Snell |
| 6,987,965 B2 | 1/2006 | Ng et al. |
| 6,991,963 B2 | 1/2006 | Krulevitch et al. |
| 7,010,356 B2 | 3/2006 | Jog et al. |
| 7,058,449 B2 | 6/2006 | Stahmann et al. |
| 7,082,333 B1 | 7/2006 | Bauhahn et al. |
| 7,110,821 B1 | 9/2006 | Ross |
| 7,127,297 B2 | 10/2006 | Law et al. |
| 7,130,692 B2 | 10/2006 | Brighton et al. |
| 7,171,166 B2 | 1/2007 | Ng et al. |
| 7,187,977 B2 | 3/2007 | Paul, Jr. |
| 7,212,854 B2 | 5/2007 | Kovak et al. |
| 7,215,991 B2 | 5/2007 | Besson et al. |
| 7,254,443 B2 | 8/2007 | Jelen et al. |
| 7,260,420 B2 | 8/2007 | Patino et al. |
| 7,295,872 B2 | 11/2007 | Kelly et al. |
| 7,298,868 B2 | 11/2007 | Comaniciu |
| 7,342,311 B2 | 3/2008 | Krulevitch et al. |
| 7,406,105 B2 | 7/2008 | DelMain et al. |
| 7,450,996 B2 | 11/2008 | MacDonald et al. |
| 7,519,431 B2 | 4/2009 | Goetz et al. |
| 7,557,433 B2 | 7/2009 | McCain |
| 7,565,195 B1 | 7/2009 | Kroll et al. |
| 7,574,262 B2 | 8/2009 | Haugland et al. |
| 7,613,518 B2 | 11/2009 | Qin et al. |
| 7,624,293 B2 | 11/2009 | Osorio et al. |
| 7,668,667 B2 | 2/2010 | Robb et al. |
| 7,769,462 B2 | 8/2010 | Meadows et al. |
| 2002/0016617 A1 | 2/2002 | Oldham |
| 2002/0193844 A1 | 12/2002 | Michelson et al. |
| 2005/0197680 A1 | 9/2005 | DelMain et al. |
| 2006/0149337 A1 | 7/2006 | John |
| 2007/0088405 A1 | 4/2007 | Jacobson |
| 2007/0123952 A1 | 5/2007 | Strother et al. |
| 2007/0142874 A1 | 6/2007 | John |
| 2007/0225770 A1 | 9/2007 | Lapanashvili |
| 2007/0239228 A1 | 10/2007 | Bradley |
| 2007/0260284 A1 | 11/2007 | Pastore et al. |
| 2009/0030484 A1 | 1/2009 | Chambers |
| 2009/0182393 A1 | 7/2009 | Bachinski |
| 2009/0247854 A1 | 10/2009 | Bordon et al. |
| 2010/0004708 A1 | 1/2010 | Jahns et al. |
| 2010/0042180 A1 | 2/2010 | Mueller et al. |
| 2010/0114211 A1 | 5/2010 | Donofrio et al. |
| 2011/0184492 A1* | 7/2011 | Martens et al. ............ 607/60 |

FOREIGN PATENT DOCUMENTS

| | | |
|---|---|---|
| EP | 1 495 783 A1 | 1/2005 |
| GB | 1093773 | 12/1967 |
| WO | WO-96/28858 A1 | 9/1996 |
| WO | WO-97/27797 A2 | 8/1997 |
| WO | WO-00/43064 A1 | 7/2000 |
| WO | WO-01/51118 A2 | 7/2001 |
| WO | WO-2004034880 A2 | 4/2004 |
| WO | WO 2007/028035 A2 | 3/2007 |
| WO | WO-2007/061233 A1 | 5/2007 |
| WO | WO-2007/117232 A1 | 10/2007 |
| WO | WO 2010/013170 A1 | 2/2010 |

* cited by examiner

METHODS AND SYSTEMS FOR REDUCING INTERFERENCE IN STIMULATION TREATMENT

INTRODUCTION

Therapists, physicians, athletes, and other individuals commonly use stimulation treatments and devices to promote physiological health. Stimulation treatments may include electrical treatments, ultrasound, massage, or any other treatment in which energy is imparted to a patient's body. Stimulation treatments may be applied to muscles, for example, in order to shape, firm, increase elasticity, refine, increase caloric expenditure, rehabilitate or redevelop. The characteristics of the stimulation, such as frequency, duration, pulse shape, and intensity, are selected to achieve different treatment goals. For example, a typical electrotherapy device is programmed to output electrical pulses at varying levels of intensity and duration to provide muscle and/or nerve stimulation.

Many stimulation systems utilize multiple channels, with multiple transducers delivering operator-specified or preprogrammed stimulation signals to electrodes or other stimulation devices. These signals may vary over time in frequency, pulse duration, current and/or voltage intensity, waveform shape, rest periods, and may also vary between channels. When multiple channels deliver stimulation pulses at approximately the same time, the pulses interfere with each other and can cause pain or other problems for the user to whom the stimulation is applied.

Stimulation interference is illustrated in FIG. 1A, which depicts a stimulation system with two stimulation channels, Channel A 102 and Channel B 104. Channel A 102 is coupled to a user by two electrodes A1 106 and A2 108, and provides pulses of stimulation current ia at a frequency denoted by FA. Channel B 104 is coupled to a user by two electrodes B1 110 and B2 112, and provides pulses of stimulation current ib at a frequency denoted by FB. FIG. 1B depicts two illustrative waveforms ia 114 and ib 116 in accordance with this scenario.

FIG. 1B also illustrates two periods of interference 118 and 120, which arise because Channels A 102 and B 104 are independent (and thus not synchronized or otherwise coordinated in time) and generate pulses within a short time frame so as to interfere. Interference effects may arise when the channels generate pulses in close proximity in time, even if not precisely simultaneously.

Interference arises in part because of energy conductive pathways present in the tissue being stimulated. When one or more energy transmissive paths exists between two or more body sites (e.g., between the sites of Channels A 102 and B 104 when applied to a user's body), the energy supplied by a stimulation signal applied at a first body site may be detectable at a different body site. This energy transmission occurs because living tissue has finite impedance. As an energy signal travels through the body, the impedance of the tissue attenuates and delays the energy signal. The amplitude, shape and other properties of a detected signal depend on a number of factors, including the stimulation signal duration, wave shape and intensity, the distance between the stimulation site and the detection site, the properties of the tissue between the stimulation site and the detection site, and other physiological and environmental variables.

Various factors may contribute to a person's experience of pain or discomfort during stimulation interference. Depending upon the frequency relation between FA and FB (see FIGS. 1A and 1B), the user may feel an intermittent intensity peak and/or stimulation modulation (e.g., a frequency and/or an intensity modulation). Any of the following conditions may affect the intensity or other aspects of a patient's sensation of stimulation interference:

- the position of the Channel A 102 electrodes with respect to the position of the Channel B 104 electrodes on the user's body—closer positions may intensify interference sensations;
- the intensity of the stimulation provided by Channel A 102 and/or Channel B 104—higher stimulation intensities may intensify interference sensations;
- relative pulse frequencies on Channels A 102 and B 104—closer frequencies (e.g., within a few parts per million or about 1%), or frequencies that are integer multiples of each other, may intensify interference sensations;
- absolute pulse frequencies on Channels A 102 and B 104—interference sensations may more likely occur during contraction-inducing stimulation (e.g., frequencies approximately 14 Hz and greater) than during twitch-inducing stimulation (e.g., frequencies approximately 10 Hz or less).

One known approach to alleviating stimulation interference involves using a central controller and synchronization system. The central controller controls and synchronizes the "firing" of stimulation pulses on Channels A 102 and B 104 to avoid stimulation interference. In some stimulation systems, Channels A 102 and B 104 are each controlled by different controllers, but are linked (wired or wirelessly) by one or more dedicated synchronization signals. FIG. 1C depicts a common stimulation system including a synchronization link 122 between Channels A 102 and B 104. In such stimulation systems, synchronization may proceed, for example, using the known synchronization pulses technique illustrated in FIG. 1D. In FIG. 1D, when a stimulation pulse 124 is completed on Channel A 102, Channel A 102 sends a synchronization pulse (not illustrated, but sent at the synchronization time marker 132) via the synchronization link 122 (FIG. 1C) to Channel B 104. The synchronization time 126 between the completion of the stimulation pulse on Channel A 102 and the receipt of the synchronization pulse at Channel B 104, which has duration tsyncAB, represents the minimum amount of time required for a pulse transmitted at Channel A 102 to be received by Channel B 104. When Channel B 104 receives the synchronization pulse from Channel A 102, Channel B 104 may then generate its own stimulation pulse 128, then transmit a synchronization pulse back to Channel A 102 (not illustrated, but sent at the synchronization time marker 134), which takes a synchronization time 130 of duration tsyncBA to arrive. If each channel waits to receive a synchronization pulse from the other channel before proceeding to deliver its own stimulation pulse, interference is avoided.

However, such a synchronization strategy may not provide optimal functionality for stimulation treatment, particularly in wireless stimulation systems. For example, if the frequencies of two channels (e.g., frequencies FA and FB for Channels A 102 and B 104, respectively) are different and not integer multiples, the timing constraints resulting from the synchronization time may impair a channel's ability to provide stimulation pulses at the desired frequency. As the number of channels increases, the timing constraints are tightened even further, impacting the frequencies at which stimulation pulses may be supplied and the precision with which stimulation at a particular frequency may be delivered. Moreover, the synchronization strategy illustrated in FIG. 1D relies on a central controller or synchronization link 122 (FIG. 1C), which can be costly, cumbersome and impractical for use in wireless and other systems with independent stimulation units.

SUMMARY

Disclosed herein are systems for providing stimulation through multiple stimulation modules. In certain implementations, these stimulation modules are capable of independent operation (i.e., without requiring the use of a central controller to time and coordinate the delivery of stimulation pulses) and are adjustable and replaceable. In certain implementations, the stimulation modules are capable of wireless communication with a microprocessor that serves as a management module used by an operator to program the independent stimulation modules and collect data from their operation.

Also disclosed herein are systems and methods for reducing unwanted stimulation interference between two stimulation modules positioned on a user's body, thereby improving stimulation treatment and other applications. The techniques described herein may be used in distributed stimulation systems (e.g., those without a central controller) or in centrally-controlled stimulation systems. These techniques advantageously involve reduced distortion of the stimulation provided by each stimulation module, and may be configured so as to only modify stimulation signals when those signals have a significant chance of causing user-perceptible interference sensations, as described in detail herein.

In one aspect, an electrostimulation system is provided and is configured with first and second transducers and a wireless management device. Each of the first and second transducers provide stimulation signals and also can detect stimulation signals provided by the other. The system includes one or more processors that are programmed to carry out methods for reducing interference between two stimulation transducers, wherein the first transducer is configured to be applied at a first body site and the second transducer is configured to be applied at a second body site. The first transducer monitors the first body site during a first detection period. During the first detection period, when a signal is detected indicative of a pulse generated by the second transducer, the first transducer delays generating a first stimulation pulse for a first delay period. If no such signal is detected, the first transducer generates the first stimulation pulse. The first transducer detects a signal indicative of a pulse generated by a second transducer by, for example, detecting a signal whose magnitude exceeds a threshold.

In another aspect, the second transducer monitors the second body site for a second detection period and when a signal is detected indicative of a pulse generated by the first transducer, the second transducer delays for a second delay period before generating a stimulation pulse. If no such first transducer pulse is detected, the second transducer generates a stimulation pulse.

In certain configurations, the system monitors the first body site at first pre-determined time intervals, which may be coupled with a first detection period and/or a first delay period, and monitors the second body site at second pre-determined time intervals with a second detection period and/or a second delay period. The time periods may be pre-determined and/or random. The first delay period may be different from the second delay period. The system may be wireless or wired.

Thresholds and indicators may also be used. For example, the system may be configured to increment a retry counter when delaying for the first delay period, and indicate a conflict (e.g., by triggering an electronic indicator) when the retry counter reaches a retry limit. Certain implementations may also generate a first marking pulse with the first transducer prior to monitoring the first body site for the first detection period, and may generate a second marking pulse with the second transducer prior to monitoring the second body site for a second detection period. In some such implementations, a signal indicative of a pulse generated with the second transducer indicates one of the second marking pulse and the second stimulation pulse.

In certain implementations, the first transducer is configured to receive and interpret a marking pulse from the second transducer that signifies a priority level of a treatment to be delivered by the second transducer. In response, for example, the processor determines the duration of the first delay period based at least in part on the identified priority level of the treatment to be delivered by the second transducer.

In certain implementations, the transducers are operatively coupled to stimulation clocks that aid in the timing of the delivery of stimulation treatment and also operatively coupled to communication clocks that aid in the timing of communication between the transducers and a management module device. In such implementations, a communication synchronization signal is sent wirelessly to one or both communications clocks and, in response to receiving the communication signal, one or both stimulation clocks are synchronized (with the communications clocks or with the other stimulation clock(s)). In certain aspects, synchronizing the stimulation clock is performed repeatedly, and a plurality of communication clock synchronization signals are received between successive stimulation clock synchronizations. In still other aspects, the number of communication synchronization signals received between successive stimulation clock synchronizations is based at least in part on a frequency of stimulation pulses generated by the first transducer.

In another aspect, a stimulation system is provided including a first processor and a first stimulation transducer device, where the first processor includes is configured to communicate with the first stimulation transducer device and manage the stimulation provided by the first stimulation transducer device. The first stimulation transducer device is configured to deliver stimulation to a user in accordance with the received information, and to detect a signal indicative of stimulation already delivered to the user by a second stimulation transducer device (a potentially interfering signal). In response to detecting an interfering signal, the first stimulation transducer device delays the delivery of stimulation.

In certain implementations, the first stimulation transducer device is configured to detect a signal during a first detection period, and if a signal is detected, delay for a delay period. After delaying the delivery of a stimulation pulse in response to detecting a signal, the stimulation transducer device allows the delivery of a stimulation pulse. In some such implementations, after delaying the delivery of stimulation, and prior to allowing the delivery of stimulation, the stimulation module allows the delivery of a marking pulse from the stimulation circuitry, which indicates to other electronic devices (attached to the user's body) that a stimulation pulse is soon to be delivered. The first stimulation transducer device may also include filtering circuitry (for, e.g., denoising, reshaping, and identifying features of detected signals) and a processor for ascribing a priority to a detected signal (for determining whether the stimulation transducer device should delay for an additional period to allow other stimulation transducer devices to deliver their pulses first). The stimulation treatment system may also include a counter for storing a value indicative of the number of times a stimulation transducer device is delayed in generating a stimulation pulse.

The stimulation treatment system may also include a second stimulation transducer device, which may be configured in any of the ways described above for the first stimulation transducer device. In certain implementations, the processor is coupled with wireless communication circuitry configured to communicate with the first (and second) stimulation transducer device, and the first (and second) stimulation transducer device includes wireless communication circuitry. In such implementations, the first (and second) stimulation transducer device is configured to receive optical or electrical signals, indicative of therapy or treatment information, sent from the first processor with the wireless communication circuitry.

BRIEF DESCRIPTION OF THE DRAWINGS

The foregoing and other objects and advantages will be appreciated more fully from the following further description thereof, with reference to the accompanying drawings wherein.

DETAILED DESCRIPTION

Described herein are many examples of stimulation interference avoidance systems and methods, which are configured to reduce unintended stimulation interference. It will be noted that the systems and methods described herein may be implemented via any suitable combination of hardware (e.g., electronic parts), firmware (e.g., software embedded in a dedicated processing device) and software (e.g., applications executed on a general purpose microprocessor or personal computer). It will also be noted that examples of electrical stimulation systems are described for ease of illustration, and that the systems and methods disclosed herein may be applied to any treatment or therapy system in which interference may occur, such as ultrasound therapy, laser therapy, thermal therapy, acoustic therapy, or any other energy-based therapy.

In some applications, the stimulation interference avoidance systems and methods disclosed herein are implemented in a stimulation system that uses wireless communication between independent stimulation modules and a management module. An exemplary wireless stimulation system will first be described, along with exemplary components of such a wireless system and exemplary transducers that may be used with the system, followed by various implementations of interference avoidance systems and techniques that may be used with the exemplary stimulation system or with other stimulation systems (e.g., wired or wireless, centrally-controlled or independent, or a combination thereof).

Wireless Stimulation Systems

Figure 1A:
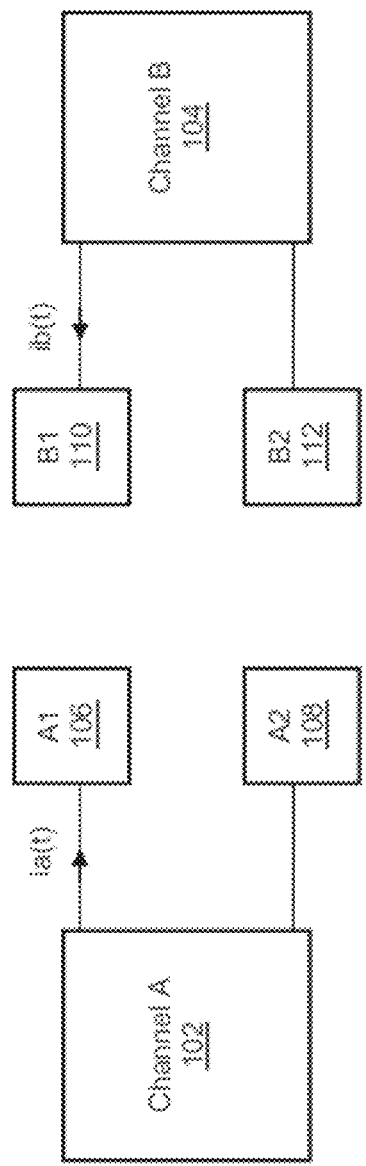
FIG. 1A is a diagram of a two-channel stimulation system.
Figure 1B:
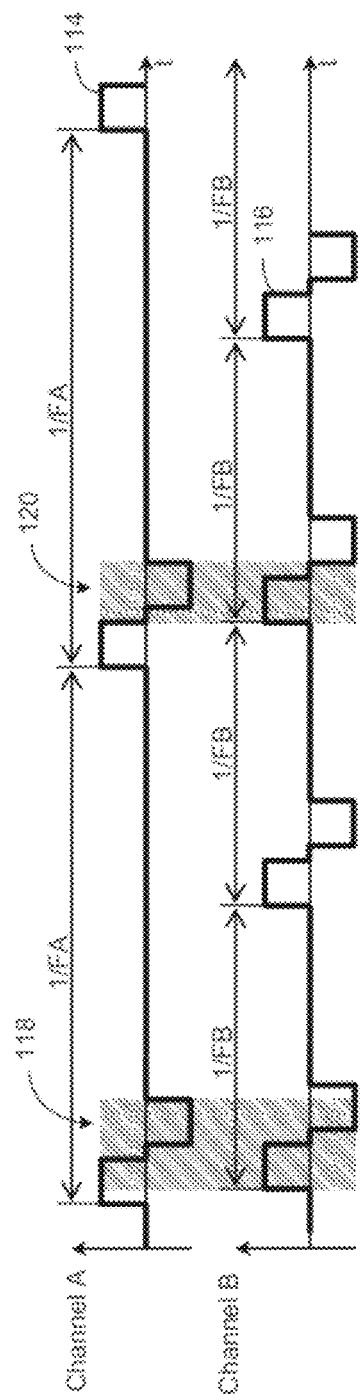
FIG. 1B illustrates interfering stimulation waveforms.
Figure 1C:
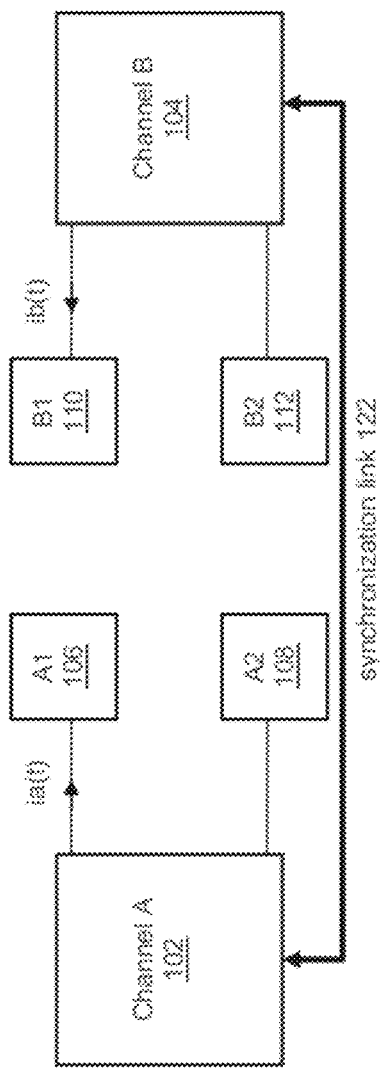
FIG. 1C is a diagram of a two-channel stimulation system with a synchronization link.
Figure 1D:
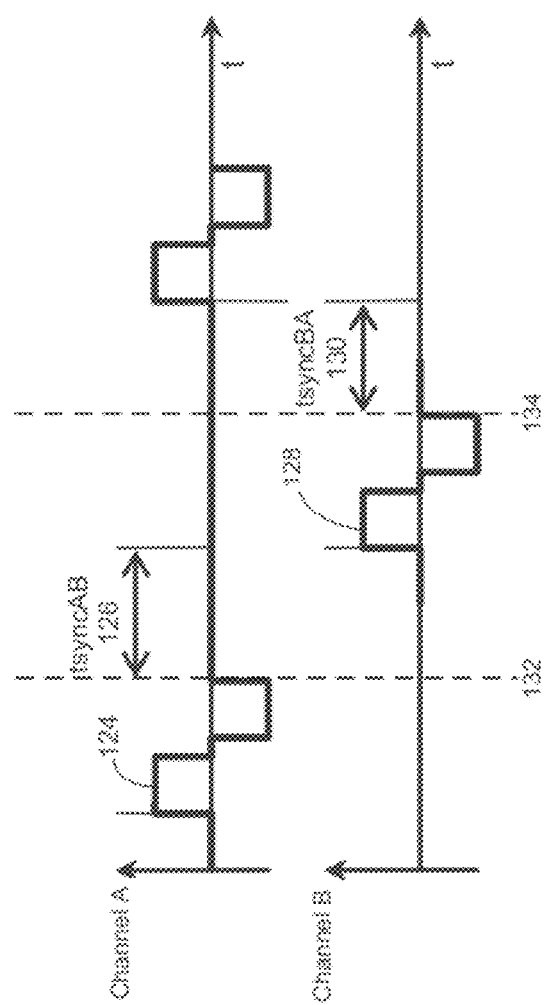
FIG. 1D illustrates synchronized stimulation waveforms that may be generated by the system of FIG. 1C.
Figure 2:
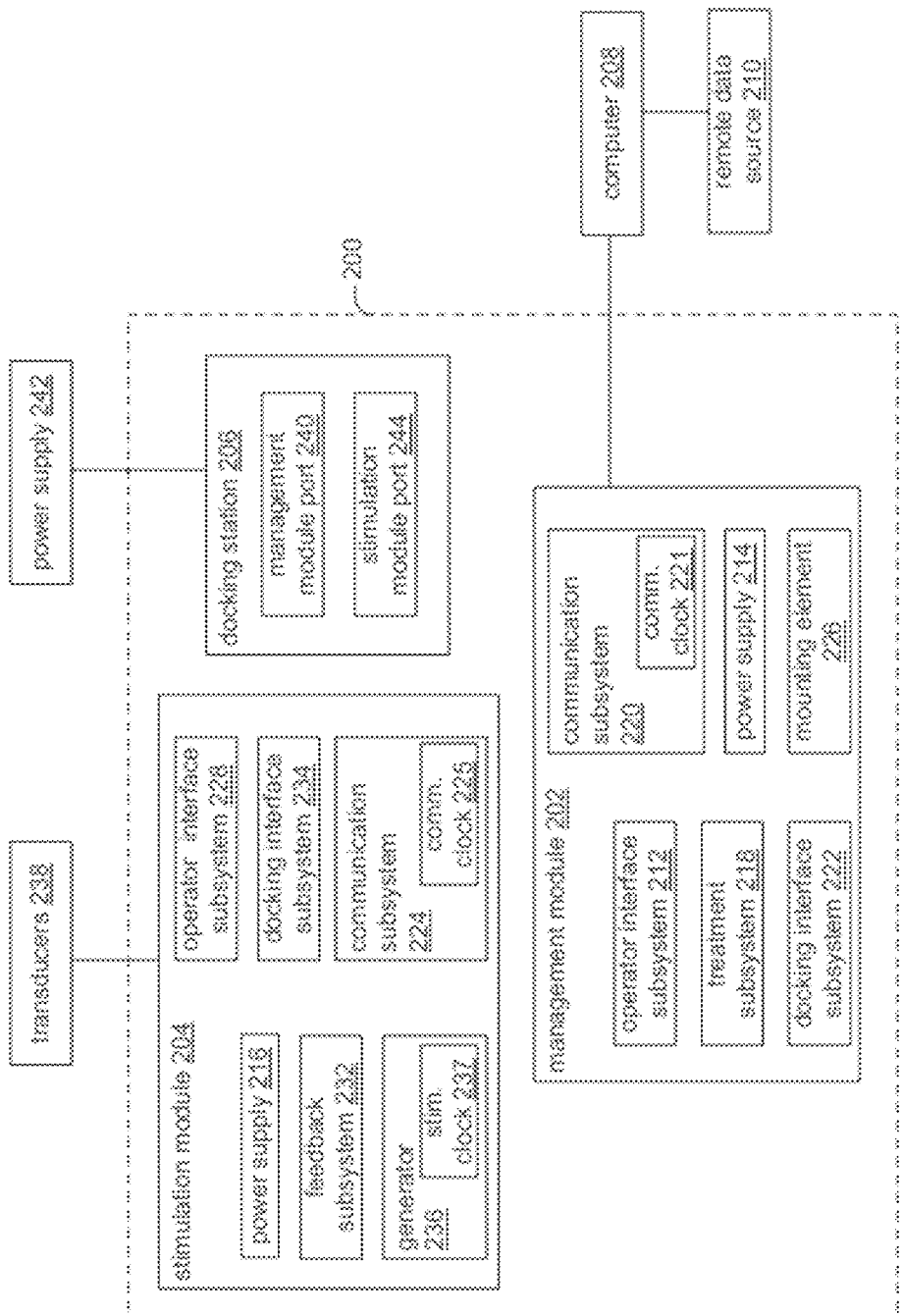
FIG. 2 is a block diagram of an illustrative stimulation system.

FIG. 2 is a diagram of a wireless stimulation system 200 that may be configured with an interference avoidance system as described herein. The stimulation system 200 includes a management module 202, a stimulation module 204 that generates and provides stimulation energy that can be used for therapeutic or prophylactic treatment, and a docking station 206. FIG. 2 also depicts a computer 208 which is configured to communicate with a remote data source 210.

The management module 202 communicates with the stimulation module 204 to specify a stimulation treatment to be provided to the user. The management module 202 uses stored programs and user inputs to determine the stimulation waveform provided to the user by specifying certain waveform parameters to the stimulation module such as amplitude, pulse duration, pulse frequency and pulse shape. The management module 202 can manage more than one output channel. In certain implementations, each output channel of stimulation is generated by a different stimulation module, such as the stimulation module 204, and each channel provides a different stimulation waveform than the other channels. Multiple channels may operate simultaneously, alternately, or in any other time-based relation. The stimulation treatment delivered by each channel may be customized and adjusted by an operator, who may be a care provider or the user him/herself. For example, an operator may control the intensity and/or energy output on each stimulation channel.

The management module 202 includes an operator interface subsystem 212 that allows an operator to select stimulation programs or protocols, set desired options and control the waveforms applied to the user. The management module 202 includes one or more processors (e.g., microprocessors) that communicate with and control the operation of the stimulation module 204, providing an interface between the stimulation module 204 and an operator managing the treatment or therapy applied to the user. The management module 202 transmits information to and receives information from the stimulation module 204 using a wireless communication protocol. The management module 202 also interfaces with the computer 208 to access the remote data source 210 and allow user control over the stimulation system 200.

The management module 202 is housed in a handheld unit with a plastic outer casing that encloses an electronics board on which are mounted the electronic components described below. The management module 202 may be waterproof or water-resistant (e.g., sweat or water are not permitted to penetrate the plastic casing), and operable with one adult hand.

FIG. 2 depicts a number of subsystems included in the management module 202. The operator interface subsystem 212 allows an operator to adjust the stimulation signals provided to a user by the system 200, view current operating parameters, view historical user data (such as performance and use statistics), view current physiological parameters (such as chemical or electrical muscle feedback signals), and adjust the capabilities of the system 200 (e.g., by downloading additional programs to the management module 202 from the remote data source 210).

The operator interface subsystem 212 may include any number of outputs, including an audible output (e.g., a speaker or buzzer), a visual display (e.g., an LCD screen or one or more LEDs), and a tactile output (e.g., a vibrating element). The operator interface subsystem 212 may include any number of user inputs, such as switches, dials, buttons, and touchpads, including non-tactile inputs such as microphones and cameras, as are commonly known in the field. In certain implementations, the operator interface subsystem 212 includes a "help" button that sends alarm signals to a personal emergency response system.

The management module 202 includes a power supply 214, which may be any suitable source of energy for powering the components of the management module 202. In certain implementations, the power supply 214 includes one or more of a battery (which may be a rechargeable battery), an AC power supply, a solar cell, a thermal cell or a kinetic cell capable of converting motion energy to electrical energy for powering the management module 202. The management module 202 may contain multiple power supplies, any of which may be any of the power supplies described herein.

The management module 202 may also include power supply monitoring circuitry (not shown). Such circuitry may monitor the power supply 214 of the management module 202 and/or the power supply 216 of the stimulation module 204. When the management module 202 and/or the stimulation module 204 does not have enough power left to complete a desired treatment or therapy, an indication is presented (e.g., on a visual display or via an audible output included with the operator interface subsystem 212) that indicates insufficient power is available. In this situation, an operator may be prohibited from accessing certain functions of the system 200 (e.g., beginning a new round of stimulation treatment).

The management module 202 (as well as any device or system component described herein) includes memory for storing basic operating parameters (e.g., pre-stored sounds, volume, display parameters, time and date) and/or supporting the subsystems described herein. In certain implementations, usage statistics are uploadable from this memory to the remote data source 210 when the management module 202 is in communication with the remote data source 210 (e.g., via the computer 208).

The management module 202 includes a number of additional subsystems, such as the treatment subsystem 218, the communication subsystem 220, and the docking interface subsystem 222. These subsystems may be configured as processor-executable code in a general or special purpose processing device (e.g., a programmable microprocessor), logic circuits, analog circuits, or any combination of hardware and software configured to provide therapeutic stimulation and perform the stimulation interference avoidance techniques described herein. The following subsystems of the management module 202 are described as separate subsystems, but the functionality of any one or more of any of the subsystems described herein may be implemented together in one or more control circuits.

The management module 202 includes a treatment subsystem 218. The treatment subsystem 218 includes circuitry for communicating with any one or more of the other subsystems and components of the management module 202, including the operator interface subsystem 212 and the communication subsystem 220. The treatment subsystem 218 includes memory for storing one or more stimulation protocols and/or programs. For example, the memory coupled to the treatment subsystem 218 may be capable of storing at least 15 different stimulation protocols or programs.

When the stimulation system 200 is being used to treat a patient, the treatment subsystem 218 generates signals that will be communicated to the stimulation module 204 (via the communication subsystem 220), instructing the stimulation module 204 to provide stimulation according to a prescribed stimulation program. As used herein, a stimulation program refers to one or more stimulation waveforms (e.g., a succession of stimulation pulses) applied for a finite period of time. For example, a program may be provided to improve a particular muscle condition, such as "endurance," "force," or "active recovery." A program may be described by any one or more of the following parameters: pulse width, pulse duration, frequency, changes in frequency, treatment duration, warm up phase parameters, work phase parameters, and recovery phase parameters. As used herein, a stimulation protocol refers to a succession of a plurality of sessions, with each session including one or more programs and/or other activities aimed at reaching a tangible goal. Examples of protocols include "firm thighs," "reduce waist," and "tone arm."

The communication subsystem 220 has a wireless receiver/transmitter which is configured for wireless communication with the stimulation module 204. This wireless communication may be an RF-based protocol, and may use a proprietary or public communications protocol. In some applications, the communication subsystem 220 communicates with the stimulation module 204 when they are spaced apart during operation of the system 200, for example, about 2 meters apart, although the system 200 may be configured for more or less separation. In some applications, the communication subsystem 220 communicates with the stimulation module 204 at up to 1 meter of separation during operation of the system 200 outdoors (e.g., with line of sight between the management module 202 and the stimulation module 204).

The communication subsystem may be separated into two or more different subsystems (e.g., one subsystem for communication between the management module 202 and the stimulation module 204 as described above, and a separate subsystem for communication between the management module 202 and the remote data source 210, each driven and controlled by different control circuits). The communication subsystem 220 includes a data port for interfacing with the remote data source 210. A data port may include a USB port for connecting a USB cable between the management module 202 and a corresponding USB port on the computer 208. In some implementations that include a computer communicably coupled between the management module 202 and the remote data source 210, the communication subsystem 220 enables the management module 202 to communicate with the remote data source 210 via the computer 208. In some implementations, the communication subsystem 220 communicates directly with the remote data source 210 without the need for an intermediate computer such as the computer 208 (e.g., via a wireless Internet or device-to-device connection such as Bluetooth).

The communication subsystem 220 maintains wireless communication with one or more stimulation modules such as stimulation module 204 (but may be wired in some implementations). The communication subsystem 220 includes at least one communication clock 221, which is an oscillator or control signal circuit that serves to coordinate the timing of communications between the management module 202 and the stimulation module 204. Additional clocks for different communication and internal operations may also be included in the management module 202. When the management module 202 loses communication with any one or more stimulation module (e.g., because of an out-of-range condition, power loss, operating error, or break in communication arising from interference with another device), all active stimulation modules (e.g., every module currently delivering or preparing to deliver a stimulation treatment) may stop, and a pause mode may begin. A display may present an operator with an opportunity to attempt to re-initialize the communication between the stimulation module and the management module 202. When communication is successfully re-established, an operator may instruct the management module 202 to re-commence any paused treatments or preparations. An operator may also abort the treatment at the time of loss of communication and/or when communication is successfully re-established.

The docking interface subsystem 222 couples the management module 202 to the docking station 206 (described in additional detail below) and recharges the power supply 214. The management module 202 also includes a mounting element 226 that allows an operator or user to position or carry the management module 202. The mounting element 226 may include any one or more of a neck band, an arm band, a waist band, an ankle band, a garment clip, an adhesive patch, or a connector attachable to any of these. A connector may be a rigid mechanical connector, a flexible connector, a hook-and-loop connector, or any other connector.

With continued reference to FIG. 2, the system 200 includes one or more stimulation modules such as the stimulation module 204 that interfaces with and drives the transducers 238 (e.g., electrodes or any other energy-delivery elements). The transducers 238 couple the stimulation module 204 to the patient. A stimulation system may include two, four, or more stimulation modules. As explained above, a plurality of stimulation modules (such as a plurality of the stimulation module 204) can be configured with an interference control system to reduce interference that may arise when the plurality of such modules are used on a single patient.

The transducers 238 may include a single transducer or more than one. In certain applications, the transducers 238 are adapted to be applied to a target site on or in a user's body. The target site may be an external surface, such as a skin surface, to provide surface or transcutaneous stimulation for non-invasive therapy applications. The target site may be an internal surface, such as a muscle or organ, in which case the transducer may be implantable.

Figure 3C:
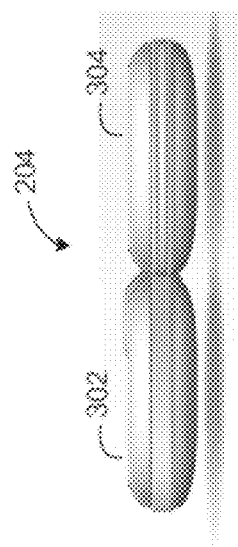
FIGS. 3A-3D depict an illustrative stimulation module.
Figure 3D:
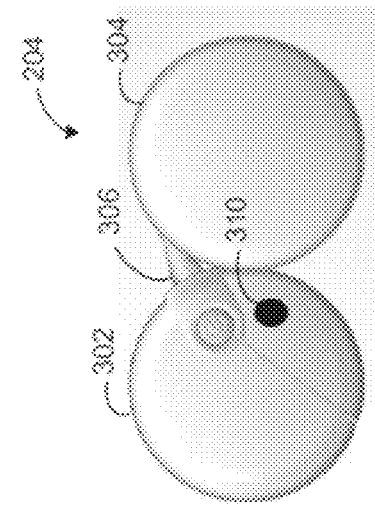
Figure 3A:
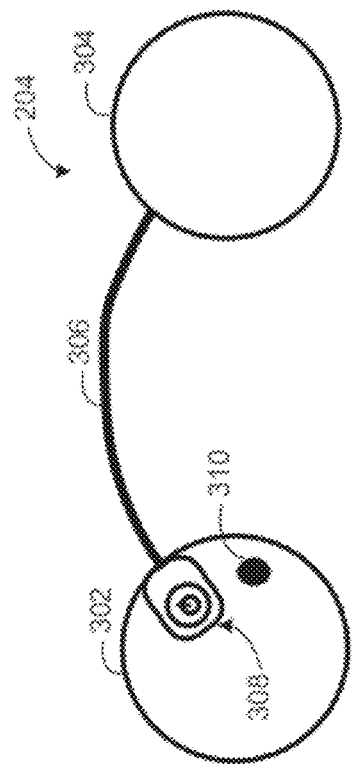
Figure 3B:
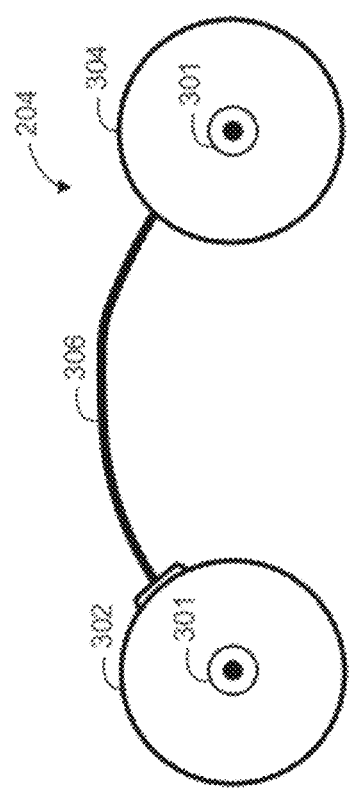

In certain implementations, the stimulation module 204 and the transducers 238 are configured within one or more housings that contain electronics and software/processing functionality, and couple with electrodes or other stimulation delivery elements. An exemplary pair of housings encasing the stimulation module 204 and the transducers 238 are depicted in FIGS. 3A-3D, in which FIG. 3A is a top view with an extended cable 306, FIG. 3B is a bottom view with an extended cable 306, FIG. 3C is a side view with a wound cable 306, and FIG. 3D is a top view with a wound cable 306. In the example shown in FIGS. 3A-3D, the stimulation module 204 includes two pods 302 and 304. Each of the two pods 302 and 304 is adapted to couple to one or more transducers 238 as described below. The pods 302 and 304 may be removably engageable from the transducers, which permits reuse of the pods with different, disposable (or reusable) transducers (FIG. 2).

The stimulation module 204 of FIGS. 3A-3D includes two pods linked by a connector, such as the flexible cable 306 that links the two pods. In other implementations, more than two pods and more than one flexible cable may be used. Each pod may be positioned at a different body site. The pods may be spaced away from each other by a fixed distance (e.g., when the pods are connected by a rigid connector), or a cable connecting the pods may be flexible to allow the pods to be positioned at any sites that are separated by any distances within the maximum cable lengths. In certain applications, the flexible cable 306 is non-elastic and supports the torsion, flexion and traction that can occur while manipulating the stimulation module 204. In certain implementations, the cable length is adjustable, with the stimulation module 204 configured to extend extra cable when necessary and retract/take up excess cable (e.g., by winding). For example, the flexible connecting cable 306 may allow a "close" pod placement on the body (e.g., approximately 6 cm between the pods 302 and 304), as well as a "distant" pod placement (e.g., approximately 25 cm between the pods 302 and 304). Side and top views of the flexible cable 306 wound around the pods 302 and 304 are depicted in FIGS. 3C and 3D.

Two or more pods may be connected by a cable, garment, bandage, or any other material, and/or electrically connected by a conductive textile, a printed conductive trace, a wire or any other conductive pathway. A stimulation module including three or more pods may have multiple connections between one or more of the pods in the module, in any suitable geometric and/or electrical configuration (e.g., a star, a line, a grid, in parallel, in series, etc.).

Figure 4A:
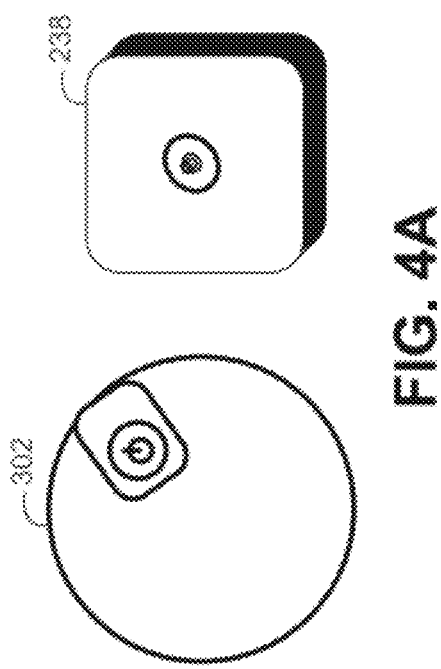
FIGS. 4A-4B depict an illustrative connection between a stimulation pod and a snap electrode.
Figure 4B:
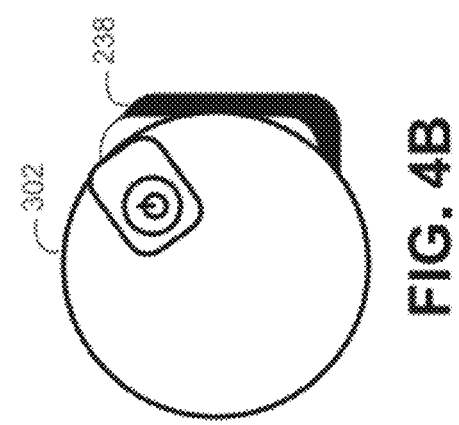

The transducers 238 may be removably engageable with the stimulation module 204, which permits reuse of the stimulation module 204 with different transducers. In certain applications, a transducer is coupled to the stimulation module 204, and the module is positioned on a user's body at a treatment site. In certain implementations, the stimulation module 204 includes one or more transducer connectors that allow connection from the side as illustrated in FIGS. 4A-4B and described in co-pending U.S. patent application Ser. No. 12/856,382 filed Aug. 13, 2010 and entitled "Low Profile Connector System," hereby incorporated by reference in its entirety herein. The transducers may include an adhesive, conductive or coupling gel, or such a gel may be applied to the treatment site or the transducer prior to treatment. The connection between the stimulation module 204 and the transducers 238 may be strong enough for the weight of the stimulation module 204 to be supported by the connection when the system 200 is in use. In some such applications, the stimulation module 204 stays in place on a user's body even when the user is running or cycling while using the system 200. The connection between the stimulation module 204 and the transducers 238 may be a proprietary connection which only permits connection between the stimulation module 204 and certain transducers (e.g., those produced by selected manufacturers). The transducers 238 and the stimulation module 204 may also be securely mounted on a user's body by a strap, garment or other attachment mechanism.

With continued reference to FIG. 2, the stimulation module 204 also includes an operator interface subsystem 228. The operator interface subsystem 228 may include any of the features described above for the operator interface subsystem 212 of the management module 202, as well as any of the additional features described below. In some implementations, the stimulation module 204 includes multiple electrode pods and all elements of the operator interface subsystem 228 are included in a single pod or are distributed over multiple pods. The operator interface subsystem 228 includes an indicator LED 310 and a mechanical press button 308 to turn the module 204 "on" and "off," as illustrated by the indicator LED 310 and mechanical press button 308 of FIG. 3A. The mechanical press button 308 is an emergency button that, when pressed during a stimulation session, stops the delivery of stimulation pulses by the stimulation module 204, and may also stop any other active stimulation modules in the system 200. In certain applications, an indicator LED included with the operator interface subsystem 228 of the stimulation module 204 indicates a "state" of the stimulation module by exhibiting distinguishing properties such as blinking or changing color. Exemplary states include "applying treatment," "interference detected" and "conflict detected" (discussed in further detail below).

The stimulation module 204 includes a communication subsystem 224. The communication subsystem 224 includes one or more microprocessors and other circuitry configured to communicate with the communication subsystem 220 of the management module 202. Communication between the communication subsystem 224 and the communication subsystem 220 may be wired or wireless or both. In certain applications, the communication subsystem 224 includes an RF receiver/transmitter for wireless communication with an RF receiver/transmitter included in the communication subsystem 220.

The stimulation module 204 may be "paired" with one or more management modules, such as the management module 202. This pairing may occur through a wired or wireless exchange of information, or by electronic or mechanical settings within one or more of the stimulation module 204 and the management module 202. In certain applications, the stimulation module 204 is paired with a corresponding management module after manufacture of the stimulation module 204. The pairing may occur before the stimulation module 204 and its corresponding management module are packaged together. After manufacture and/or sale, the management module 202 may be paired with new or replacement stimulation modules by automatic detection and/or by a command issued by an operator through the operator interface subsystem 212. The communication subsystem 224 includes at least one communication clock 225, which is an oscillator or control signal circuit that serves to coordinate the timing of communications between the stimulation module 204 and the management module 202. Additional clocks for different communication and internal operations may also be included in the stimulation module 204.

The stimulation module 204 includes a generator 236 that provides energy to one or more of the transducers 238 in accordance with the stimulation regimen or protocol specified by the management module 202. The generator 236 includes circuitry for receiving energy from the power supply 216, circuitry for transforming the received energy into the waveform specified by the management module 202, and circuitry for transmitting the transformed energy to one or more of the transducers 238. The generator 236 includes a stimulation clock 237, which is an oscillator or control signal circuit that serves to serves to time and trigger the stimulation treatment provided by the stimulation module 204. The generator 236 may be separate from the transducers 238, or some or all of the components of the generator 236 may be integrated with the transducers 238. In certain applications that include electrical stimulation, the generator 236 is capable of supplying energy to the transducers 238 to provide waveforms with some or all of the following characteristics:

square, symmetrical, and/or compensated waveforms;
up to approximately 120 mA current deliverable in an impulse under a specified body load;
pulse widths between approximately 60 and 400 µs; and
pulse frequencies between approximately 1 Hz and 150 Hz.

The power supply 216 included in the stimulation module 204 can take the form of any of the examples described above with reference to the power supply 214 of the management module 202, or any other suitable power supply. In implementations in which the stimulation module 204 includes one or more pods, a first pod may include the power supply 216 (e.g., as a battery).

The stimulation module 204 includes a feedback subsystem 232. The feedback subsystem 232 provides indications of the user's physiological characteristics and/or the response of a user's body to applied stimulation. In certain implementations, the feedback subsystem 232 detects stimulation applied by other stimulation modules at different body sites (e.g., by sensing voltage, current, or motion). In some such implementations, the feedback subsystem 232 is included in the generator 236, and may share a portion of the circuitry used by the generator 236. In some implementations, the feedback subsystem 232 is integrated with the transducers 238. The feedback subsystem 232 provides feedback to an operator via the operator interface subsystem 228 of the stimulation module 204, the operator interface subsystem 212 of the management module 202, or the remote data source 210. The feedback subsystem 232 measures or detects a user's characteristics and/or response and may do so by detecting electrical signals using a connected electrode, mechanical signals using a piezoelectric sensor or accelerometer, chemical signals using a chemosensor, or any other known physiological sensor. The feedback subsystem 232 provides feedback about the user to the management module 202 via the communication subsystem 224.

The feedback subsystem 232 includes a feedback sensor for measuring or detecting a user's characteristics and/or response to stimulation. This feedback sensor may include one or more electrodes, which may also be used as the transducers 238 to deliver electrical stimulation to the user. The feedback sensor may register the mechanical signals of stimulated tissue using a piezoelectric sensor or accelerometer, which may provide feedback of muscle characteristics and activity. The feedback sensor may monitor any user characteristics, including optical and chemical properties. A feedback sensor may also receive signals from a user input, through which a user can indicate pain, relief of pain, fatigue, or any treatment response. In implementations in which the stimulation module 204 includes multiple pods, a pod containing the feedback sensor may be visually differentiable from other pods to facilitate placing the feedback sensor on a correct muscle motor point or other body site (e.g., a pod including a feedback sensor may be larger and/or differently-shaped). For example, the feedback sensor may be a motor point pen that is removably engageable with the stimulation module 204.

The feedback subsystem 232 may provide feedback using the Mi-technology approach developed and commercialized by Compex Technologies. In such implementations, an automatic cronaxy measurement is made by one or more stimulation modules included in the system 200. In certain implementations, an automatic cronaxy measurement is made by just one stimulation module 204 included in the system 200, and an operator has the option to select which of multiple stimulation modules will make the measurement. An operator may extend this function to additional channels by interacting with the remote data source 210. Additional Mi-applications developed by Compex Technologies, such as Mi-Action, Mi-Range or Mi-TENS may be included in the system 200 or added to the basic functionality of the system 200 (e.g., by accessing the remote data source 210 to download additional functionality).

The stimulation module 204 includes a docking interface subsystem 234 to couple the stimulation module 204 to the docking station 206. The docking station 206 includes a management module port 240 and a stimulation module port 244, which may be used to dock one or more management modules and one or more stimulation modules, respectively, and may include circuitry for transforming energy from a power supply 242 into a form that is suitable for recharging the management module 202 and the stimulation module 204 through the respective ports. The docking station 206 may also include circuitry for receiving information from one or more of the management module 202 and the stimulation module 204 (e.g., usage information, status information and diagnostic information). The docking station 206 may provide a validation indicator when a stimulation module 204 is properly interfaced with a stimulation module port 244 (e.g., by sounding a tone or illuminating an LED).

The system 200 is configured to connect to a remote data source 210. In the implementation of FIG. 2, this connection occurs through an intermediate connection with a computer 208. At least one of the computer 208 and the remote data source 210 provides additional features and functions to the system 200. In certain implementations, the remote data source 210 is a web server and the computer 208 mediates between the management module 202 and the remote data source 210. For example, the computer 208 may present a web interface to an operator which allows the operator to perform any one or more of the following operations:

navigate through a number of stimulation protocols and choose which ones he/she would like to download to the management module 202;
customize the planning of protocols (e.g., by adjusting the frequency of the sessions and the days and time of occurrence);
customize a voluntary training calendar;
see statistics of stimulation usage; and
set preferences (e.g., desired language).

Figure 5:
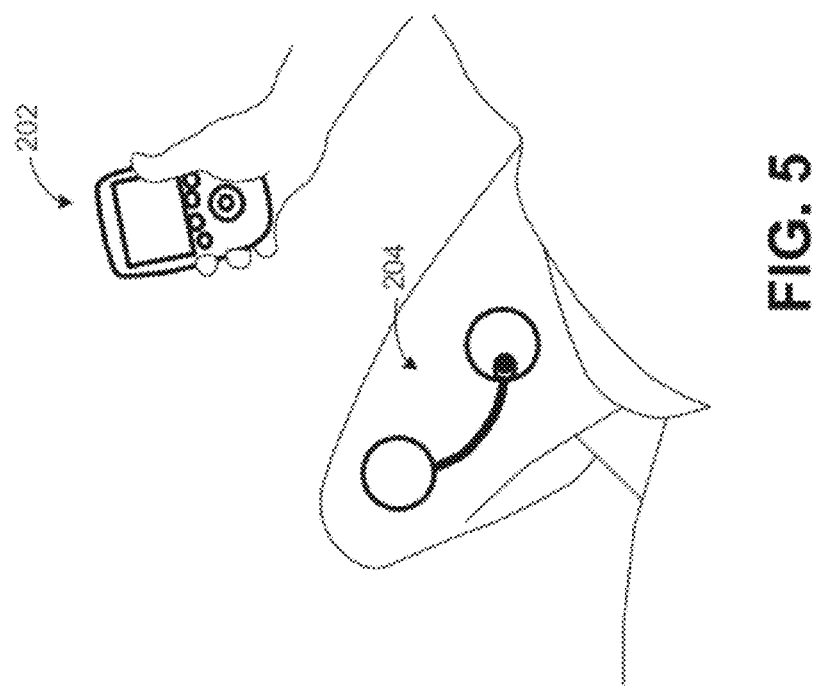
FIG. 5 illustrates the use of an electrical stimulation system on a user's body.

The management module 202 may be configured for at least three modes of operation: a "use mode," a "charge mode" and a "programming mode." In "use mode," an operator navigates through menus displayed by the operator interface subsystem 212 and selects a protocol or program. Once a protocol or program is selected, and after placing the stimulation module 204 and attached transducers 238 on the user's body, a stimulation session begins. FIG. 5 illustrates the system 200 in use on a patient's body. The management module 202 uses communication subsystem 220 to communicate and exchange information wirelessly with the stimulation module 204 before stimulation (and may communicate during or after stimulation). In some applications, the management module 202 communicates with the stimulation module 204 prior to treatment to communicate the parameters of the desired stimulation treatment. The stimulation module 204 then supplies the stimulation treatment according to those parameters without requiring additional control signals from the management module 202. Information such as actual time, network quality (i.e., the quality of the communication between the management module 202 and all connected stimulation modules) and the power level of the power supply 214 may be displayed on a display included with the management module 202. If a transducer default is detected during a stimulation session, all the active stimulation modules may cease to supply stimulation treatment and the management module 202 may enter a pause mode. A display included with the management module 202 may identify one or more channels on which the electrode default has been detected.

In "charge mode," the management module 202 and the stimulation module 204 are placed in the docking station 206 and may recharge their power supplies 214 and 216, respectively. The management module 202 may provide an indication when the components of the system 200 are charging, and a different indication when the components of the system 200 are fully charged (e.g., via a display included in the operator interface subsystem 212).

In "programming mode," the management module 202 is connected to the computer 208 via an USB cable, as discussed above. The computer 208 is, in turn, connected to the remote data source 210 (e.g., via a remote communication protocol, such as an Internet or Ethernet protocol). An operator may use the management module 202 and/or the computer 208 to obtain features and functions made available by the remote data source 210, including viewing new protocols or establishing a treatment program. An operator may also download new protocols and new settings to the management module 202 from the remote data source 210. In the programming mode, information may be transferred from the computer 208 to the management module 202. Information transferred from the computer 208 to the management module 202 may include any one or more of:

selected protocols to be downloaded to the remote;
a text library in a specified language;
customized planning (stimulation and treatment program planning); and
new user settings, date and hour, new icons and logos.
In the "programming mode," information is transferred from the management module 202 to the computer 208. Information transferred from the management module 202 to the computer 208 may include any one or more of:

state of usage of the programs/protocols in the management module 202;
statistics of the used programs/protocols;
programs/protocols embedded in the management module 202;

ID of the management module 202 and the user/operator; power supply level; and settings of the management module 202.

Stimulation Interference Avoidance Systems

Having described examples of stimulation systems, exemplary implementations of stimulation interference avoidance systems are now described. As discussed above, the system 200 may include multiple stimulation modules such as the stimulation module 204. Each module is placed at a particular location on a user's body and delivers one or more channels of stimulation treatment. For ease of illustration, the following discussion describes systems and methods in which two stimulation modules are used during a stimulation session, with each module providing one channel of stimulation, but it will be understood that the challenges and solutions discussed herein may be applied to stimulation systems in which two or more stimulation channels are used. In certain treatment settings, three or more channels of stimulation may be advantageous; for example, certain muscle stimulation treatments for gait regulation may benefit from three, four or more channels of stimulation.

Figure 6A:
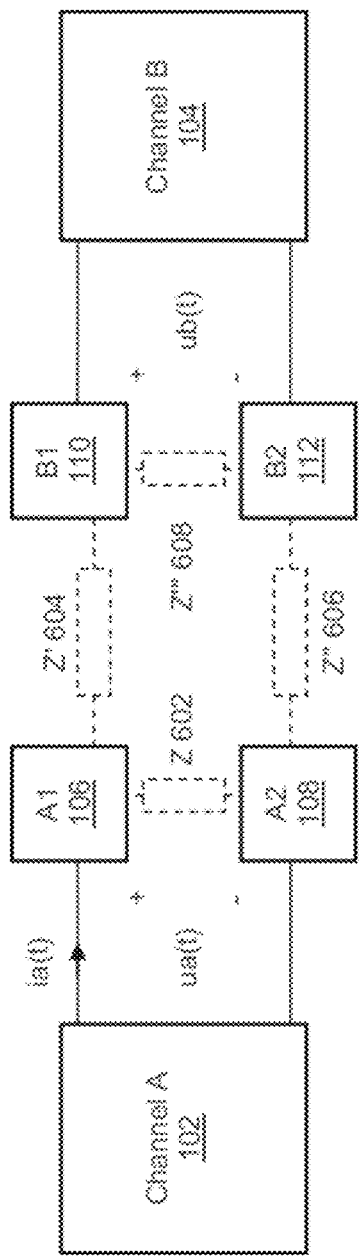
FIG. 6A is a diagram of a two-channel stimulation system applied to a user's body.

The stimulation interference avoidance systems described herein include processing devices that, in preferred implementations, are stored within the housing of stimulation hardware, such as the stimulation module 204, and are configured to receive and process electronic signals indicative of energy transmitted through a patient's tissue. FIG. 6A illustrates a two-channel stimulation system applied to a user's body that can be configured with a stimulation interference avoidance system. A stimulation signal delivered by electrode A1, for example, may travel through the patient's tissue and reach electrode A2, and also may travel to electrodes B1 and B2. The freedom of the signal energy to traverse these pathways depends on the impedance of the tissue through which the signal energy passes. As shown, the energy transmissive pathways through the patient have impedances indicated by the impedances Z 602, Z' 604, Z" 606 and Z''' 608, which are connected between and across the Channels A 102 and B 104.

In the configuration illustrated in FIG. 6A, two pairs of electrodes are shown. The first pair of electrodes delivers the Channel A 102 stimulation pulses, and a second pair of electrodes delivers the Channel B 104 stimulation pulses. In some applications, within each pair, one electrode is designated as the "active" electrode (e.g., a source of medicament) and the other electrode is the "return" electrode (e.g., the receiving electrode or reservoir of treatment-neutral molecules in iontophoretic treatment). In some applications, such as ultrasound stimulation systems, a single transducer per channel is sufficient.

As shown in FIG. 6A, the first pair of electrodes (A1 106 and A2 108) delivers a current ia to a user's body. Because the user's body exhibits impedance along the conductive pathways between the electrode A1 106 and the electrode A2 108, the applied current ia will induce a voltage difference ua between the electrodes A1 106 and A2 108. This phenomenon may also be characterized as a current ia induced by an applied voltage difference ua between the electrodes A1 106 and A2 108. An example waveform for ia is illustrated as the stimulation pulse 610 in FIG. 6B, and an illustrative induced voltage signal ua taken between the electrodes A1 106 and A2 108 is shown as the voltage signal 612 of FIG. 6B.

Figure 6B:
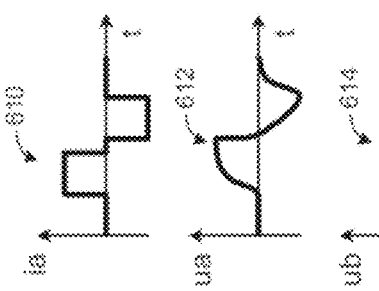
FIG. 6B illustrates current and voltage waveforms that may be generated and detected by a two-channel stimulation system in accordance with the diagram of FIG. 6A.
Figure 6B:
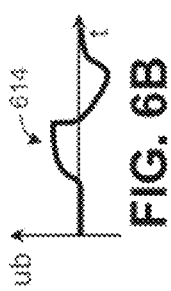

Because of the energy transmissive pathways through the user's body between the terminals of Channel A 102 and Channel B 104 (represented by impedances Z 602, Z' 604, Z" 606 and Z''' 608), the current stimulation pulse is results in a voltage signal ub across the two electrodes B1 110 and B2 112 of Channel B 104. An illustrative voltage signal 614 is depicted in FIG. 6B. The shape, amplitude and other characteristics of the voltage signal ub depend on the characteristics of the stimulation pulse and on the impedances Z 602, Z' 604, Z" 606 and Z''' 608. As noted above, a stimulation signal delivered to one body site may be detectable at another body site due to energy transmissive pathways between the channels through the user's body. If a stimulation pulse is generated on Channel B 104 near to when a stimulation pulse is generated on Channel A 102, it is possible that the pulses will interfere within the user's body and cause discomfort or pain. Therefore, the system of FIG. 6A can include processors configured to detect such nearby stimulations and avoid generating interfering stimulation pulses, thus reducing unintended and potentially harmful stimulation interference.

Figure 7:
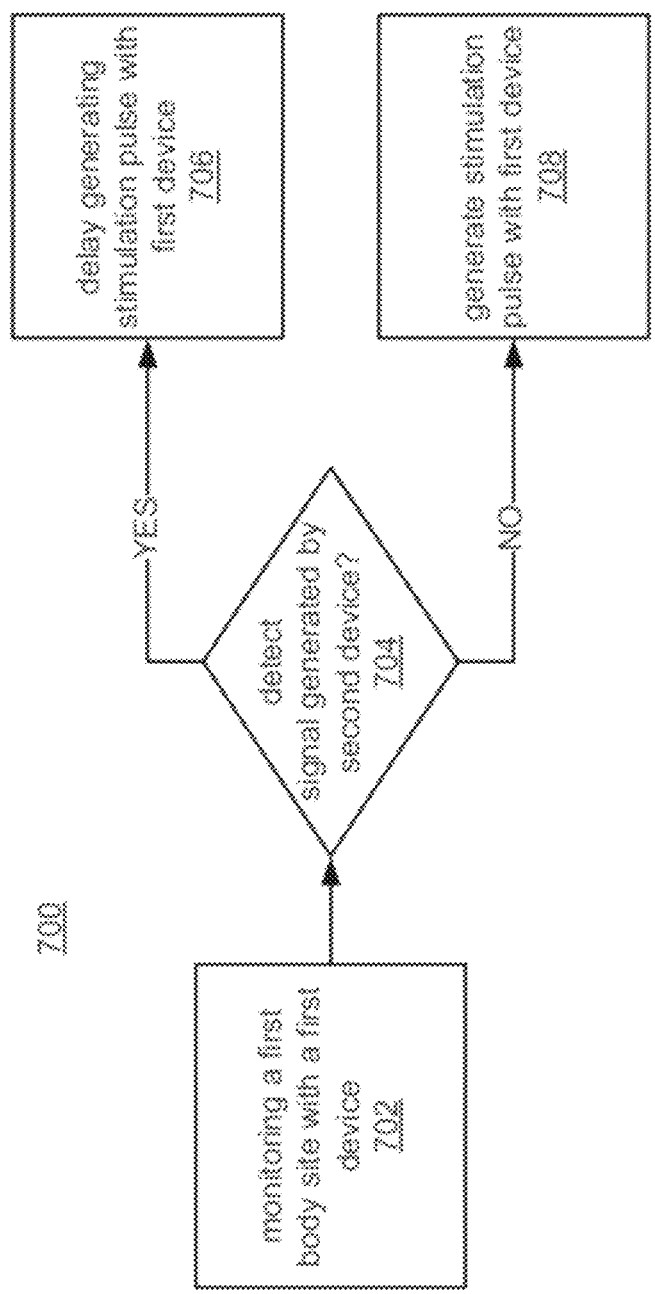
FIG. 7 is a flow diagram of the operation of a stimulation interference avoidance system.

FIG. 7 is a flow diagram 700 of the operation of such a stimulation interference avoidance system. Each stimulation module 204 of the system 200 (FIG. 2) includes microprocessor circuitry configured for carrying out the stimulation interference avoidance process illustrated by the flow diagram 700. Execution of this process in a stimulation module may be performed by any combination of dedicated hardware (e.g., semiconductor logic circuits configures appropriately and printed on a circuit board), firmware (e.g., dedicated software embedded in a programmable processor) and software (e.g., applications installed and executable on a general purpose processor). The stimulation interference avoidance process of the flow diagram 700 is sometimes described as being performed by a stimulation module, but any one or more components of a stimulation system may be configured to perform one or more of the desired steps. For example, the step 702 may be performed by a monitoring device (e.g., an electrode system configured for sensing electrical signals) and the step 704 may be performed by a management module (e.g., with processors configured for analyzing the sensed electrical signals). The following discussion of the flow diagram 700 addresses several such exemplary devices.

At the step 702, a first device, such as the stimulation module 204 (FIG. 2), begins to monitor a first body site. The first device monitors the first body site by measuring one or more signals indicative of a stimulation pulse (e.g., a voltage, current, pressure, motion, temperature, radiation or other signal) or a signal indicative of a patient response to a stimulation pulse (e.g., a nervous response, a muscle response, a movement response, a pain response, etc.). In certain implementations, the first device monitors the first body site by receiving voltage signals across two or more electrical terminals. In certain implementations, sensing terminals are used to receive the voltage signal and also apply electrical stimulation pulses to the first body site. Alternatively, the system may have terminals dedicated to receiving and monitoring a voltage signal, and different terminals to apply stimulation signals to the user's body.

The step 702 may be performed periodically at a particular frequency, which may be greater than, less than, or equal to the frequency of stimulation applied by a stimulation module, or at pre-determined time intervals. The step 702 may be performed at random intervals, at a changing frequency (e.g., a modulated frequency that varies between a lower frequency and an upper frequency), or in response to commands from a management module (e.g., the management module 202 of FIG. 2) or from an operator. The monitoring that begins at the step 702 is performed over a stimulation activity detection period with a duration denoted by Tsad. The stimulation activity detection period may have a pre-determined, fixed duration, a random duration, a combination of fixed and random durations, and may include two or more non-contiguous time intervals. Moreover, the time intervals at which the step 702 is performed and the duration of the stimulation activity detection period may be different for different stimulation modules executing the step 702. The duration of the stimulation activity detection period may change in response to user or environmental conditions detected by the first device. In some applications, Tsad is increased when the first device detects an increase in noise in one or more monitored signals. In some applications, Tsad is decreased when other stimulation modules are detected (as discussed below with reference to the step 704) or a conflict occurs (as discussed below with reference to the step 706).

In certain applications, each stimulation module performs the step 702 prior to providing a new stimulation pulse by measuring a voltage signal ux over a stimulation activity detection period of duration Tsad. The duration Tsad may vary between different stimulation modules. This measurement is taken across the stimulation module's stimulation electrode terminals (or, in some applications, across alternate voltage measurement terminals). The monitoring that begins at step 702 may include storing received signal data in a buffer or other memory. The step 702 includes signal processing steps, performed by any appropriately-configured circuitry included in the first device (such as a DSP chip). Examples of signal processing steps include upsampling, downsampling, interpolating, determining statistics (e.g., means, modes, maxima, minima, standard deviations), time windowing, removing outliers, filtering (e.g., high-, low-, band-pass or notch filtering), transforming into a spectral domain, calculating energy and/or power in a time or frequency interval, correlating, detecting peaks, shape matching, FIR or IIR filtering, or any combination thereof. The step 702, as well as any processing or filtering described herein, is performed by software, hardware, or a combination of software and hardware.

At the step 704, the first device determines whether a signal is present that is indicative of a stimulation pulse generated by a second device. Such a signal will be referred to as a "significant signal." The second device may be a stimulation module like the stimulation module 204 (FIG. 2). The significant signal is detected in the signal or signals received by the first device during monitoring of the first body site at the step 702. As explained in additional detail below, the first device will either "fire" a stimulation pulse, or delay (and then fire), depending on whether the first device detects a significant signal.

In certain implementations, the system is configured so that it directs a firing or delay depending on whether a detected signal is significant. Determining whether a significant signal is present may employ any one or more known detection, estimation and pattern recognition techniques: for example, hypothesis testing, a decision tree, maximum likelihood detection, pattern matching, principal components analysis, correlations, total transmitted power, shape matching, frequency analysis, wavelet analysis, statistical likelihood techniques, etc. In certain implementations, processing circuitry in a stimulation module is configured to analyze a monitored signal and use a threshold test to determine whether a significant signal is present. An exemplary threshold test includes the following assessment:
  a. if the intensity of the monitored signal remains within a first range, no significant signal is detected.
  b. if the intensity of the monitored signal exceeds the first range, a significant signal is detected.

The intensity of a monitored signal refers to any one or more of amplitude, magnitude, energy, power, or duration over any time intervals or frequency bands. The first range may be a symmetric range (e.g., a current amplitude within [−5 mA, +5 mA]), an asymmetric range (e.g., a current amplitude within [−2 mA, +4 mA]), or include multiple non-contiguous intervals (e.g., a power within [0 mW, 1 mW] or [4 mW, 6 mW]). In certain implementations, the monitored signal is a voltage ux and the first range is [−Vth, +Vth], where Vth is a pre-determined voltage level. A significant signal is detected when the voltage signal ux has an amplitude outside the first range. In some applications, the voltage ux is monitored by the electrode terminals of a stimulation module, as discussed above. More than one significant signal may be detected at the step 704. For example, two or more significant signals may be spaced apart in time, or two or more significant signals may be of different modalities (e.g., a voltage signal and a chemo-detector signal).

The first device may use dynamic criteria at the step 704 to determinate whether a significant signal is present. In noisy sensing conditions (e.g., in the presence of ambient electrical noise from surgical instruments, or when other monitoring/treatment devices are in contact with the patient), the first device may implement a threshold test as described above and may dynamically adjust the thresholds required for detection of the significant signal. Examples of dynamic adjustments include raising an amplitude threshold or an energy threshold in response to a higher noise floor. Dynamic criteria may be implemented as dynamic signal processing steps. For example, filtering applied to a monitored signal may depend on the frequency characteristics of the environmental noise impinging on the monitored signal. In the presence of a strong 60 Hz component (e.g., from other electrical devices operating near the user, such as electrosurgical devices), the first device may selectively apply a 60 Hz notch filter or other suitable filter to remove this frequency component before determining whether a significant signal is present.

As shown in the flow diagram 700 of FIG. 7, if the first device does not detect a significant signal at the step 704, the first device proceeds to generate a stimulation pulse at the step 708. In some implementations, the first device instructs another device to generate the stimulation pulse at the step 708. In certain applications, circuitry included with the stimulation module 204 causes the generator 236 (FIG. 2) to generate the stimulation pulse at the step 708.

However, if the first device detects a significant signal at the step 704, the first device delays generating the stimulation pulse at the step 706. In certain implementations, the delay lasts for a duration of time denoted by Tpd, as programmed into the microprocessor and controlled thereby. The duration Tpd may be pre-determined, fixed or variable, and may depend upon any of the factors discussed above for the stimulation activity detection period Tsad. Additionally, the duration Tpd may be determined based at least in part on characteristics of the significant signal detected at the step 704. For example, the value of Tpd may increase from a nominal or baseline value when the significant signal has an energy or magnitude that exceeds a threshold (which may be a different, higher threshold than the threshold used in a threshold test included as part of the significance test at the step 704), while the value of Tpd decreases from a nominal or baseline value when the significant signal has an energy or magnitude that is below a threshold (which may be a different, lower threshold than the threshold used in a threshold test included as part of the significance test at the step 704). In another example, the value of Tpd increases from a nominal or baseline value when more than one significant signal is detected at the step 704. The duration Tpd may include a random component, as generated by a pseudo-random number generator within the processing circuitry of the first device. The random component of Tpd may be selected from within an allowable range of random time periods defined by a lower duration limit and an upper duration limit (e.g., 1-1000 μs).

In certain implementations, after the first device delays at the step 706, it then proceeds to generate a stimulation pulse as described above with reference to the step 708. In other implementations, after the first device delays at the step 706, it "retries" by returning to step 702 and executing steps 702 and 704. In such implementations, when the number of retries reaches a retry limit (e.g., ten retries as counted by a retry counter variable stored in a memory in the first device or another device, such as a management module), the first device registers an error condition, which may prompt an operator alert. An electronic indicator (such as an LED, a display screen, a piezoelectric buzzer or an electronic memory) may be used to store the error condition or alert an operator. Such an error condition may be considered a "conflict" between the first device and at least one other stimulation device causing the detected significant signals. The likelihood of conflicts depends on one or more of several factors, including the number of stimulation devices in operation (e.g., the number of stimulation channels delivering stimulation signals), the stimulation frequency of each channel (e.g., the instantaneous frequency of a channel during a treatment or therapy in which the frequency changes over time) and the pulse duration of each channel (e.g., the duty cycle of stimulation delivered by each channel). In certain implementations, the number of retries required before registration of an error condition is not fixed, but instead depends on an acceptable amount of delay that can be tolerated by the first device. For example, when the first device is configured to separate delivered stimulation pulses by a nominal period, the first device may tolerate "skipping" a certain number of stimulation pulses when significant signals from other stimulation modules are detected. In such implementations, the number of retries allowed before registering an error condition depends on the number of retries that can be attempted in the time it would have taken the first device to generate the certain number of "skipped" pulses, which may in turn depend on Tsad and Tpd. In some implementations, a retry counter is included in a management module, or a signal is transmitted (e.g., wirelessly) from the first device to a management module when a conflict occurs.

When two or more stimulation devices are in operation, and each stimulation device is executing an interference avoidance process like the process illustrated by the flow diagram 700 of FIG. 7, multiple stimulation devices may detect each other and, in response, the multiple stimulation devices may delay their respective stimulation pulses for approximately the same delay period Tpd. This situation may lead to additional conflicts. To avoid such conflicts, the delay period of different channels are preferably programmed to have different durations Tpd. For example, the delay time of Channel A 102 may be pre-programmed to be shorter than the delay time of Channel B 104 (FIG. 6A). In some implementations, the delay time Tpd for each channel is calculated as the sum of a fixed time (which may be common to all channels) and a random time generated for that channel (e.g., as generated by a pseudo-random number generation circuit communicable with the device delivering stimulation for that channel). Further, as discussed above (e.g., with reference to the step 706), the ability of a stimulation device to generate pulses at desired time intervals may be impacted by time delays that result from the interference avoidance steps described herein. The variation of the actual stimulation delivery schedule around a nominal, desired stimulation schedule may be referred to as "jitter." Different stimulation applications may impose different therapeutically-acceptable limits on jitter, which in turn lead to allowable ranges for interference avoidance technique parameters such as Tsad, Tpd, and the maximum allowable number of retries. These allowable parameter ranges are determined by any of a number of techniques, including mathematical approximation methods, physiological constraints, and simulation-based methods.

As discussed above, the exemplary interference avoidance techniques described herein can be implemented in a detection system configured with a first device that detects a signal indicative of a pulse generated by a second device. In certain embodiments, the interference detection system is also used to assist in proper placement of the electrodes or other transducers. For example, good contact between the second device and the patient's body can be confirmed when the second device also detects the signal indicative of a pulse generated by the second device (e.g., an electrical pulse generated by one electrode attached to a patient's body can be detected at the same electrode or a different electrode on the same device). When the second device detects this signal, a positive body site contact condition for the second device is registered by the stimulation system. In certain implementations, registering a positive body site contact condition is required before the second device is allowed to generate stimulation pulses, in order to prevent stimulation pulses from being delivered to transducers that are not in contact with a patient's body (i.e., an open circuit-like condition exists between the transducers). In such implementations, once a positive body site contact condition is registered by a device, that device may proceed to generate a stimulation pulse.

Figure 8:
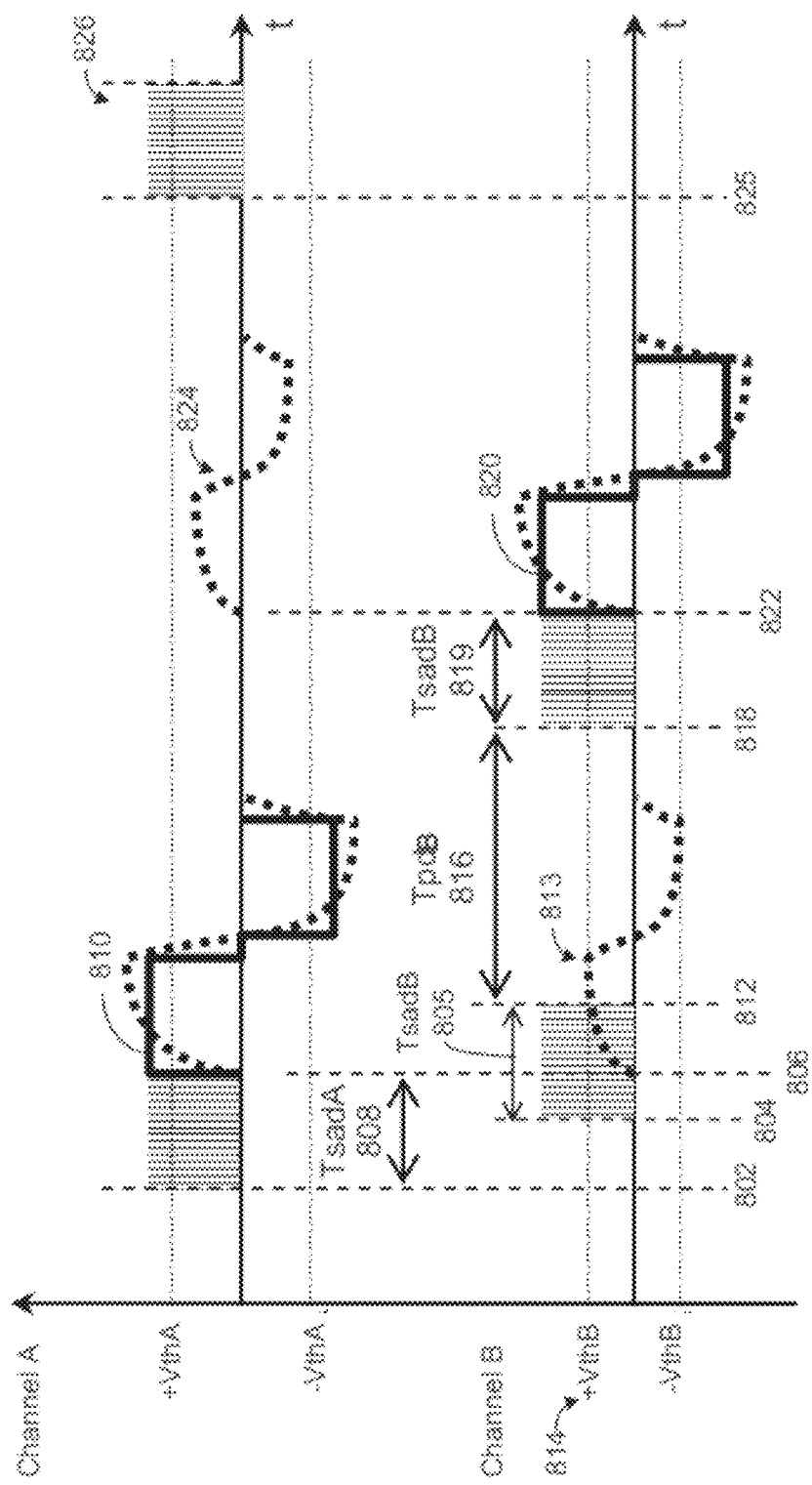
FIG. 8 depicts non-interfering stimulation waveforms that may be generated by a system implementing the technique of FIG. 7.

FIG. 8 depicts exemplary waveforms that are generated by a stimulation interference avoidance system operating according to the process illustrated by the flow diagram 700 (FIG. 7). In particular, FIG. 8 depicts an example pair of waveforms that are generated by Channels A 102 and B 104 (and controlled by stimulation modules A and B, respectively, each implementing the process of FIG. 7). At the time 802, stimulation module A begins making a voltage measurement over a stimulation activity detection period 808 of duration TsadA on Channel A 102 to detect stimulation signals generated on other channels. At the time 804, a stimulation module B begins making a voltage measurement over a stimulation activity detection period 805 of duration TsadB on Channel B 104. At the time 806, since no activity was detected by the stimulation module A during its stimulation activity detection period 808, the stimulation module A generates a stimulation pulse 810 on Channel A 102 (in accordance with the step 704 of FIG. 7). At the time 812, Channel B 104 senses the stimulation pulse 810 generated on Channel A 102 by a voltage measurement that reaches a detection threshold (+Vth 814), indicating a significant signal from Channel A 102 has been detected. The stimulation module B consequently delays beginning another stimulation pulse for a period 816 of duration TpdB (in accordance with the step 708 of FIG. 7). At the time 818, after the duration TpdB delay period 816, stimulation module B begins again to measure stimulation activity voltages over a stimulation activity detection period 819 of duration TsadB. As shown, no signal is detected by the stimulation module B that exceeds the threshold range [−Vth, +Vth] during the period 819. Accordingly, stimulation module B proceeds to generate its stimulation pulse 820 at the time 822. As a result of the stimulation pulse generated by the stimulation module B, a voltage signal 824 appears across the electrode terminals of Channel A 102 (and could be actively measured by the stimulation module A, if desired). At the time 825, the stimulation module A begins again to monitor for an opportunity to generate another stimulation pulse, and thus begins a new stimulation activity detection period 826 using the Channel A 102 terminals, repeating the cycle.

Figure 9:
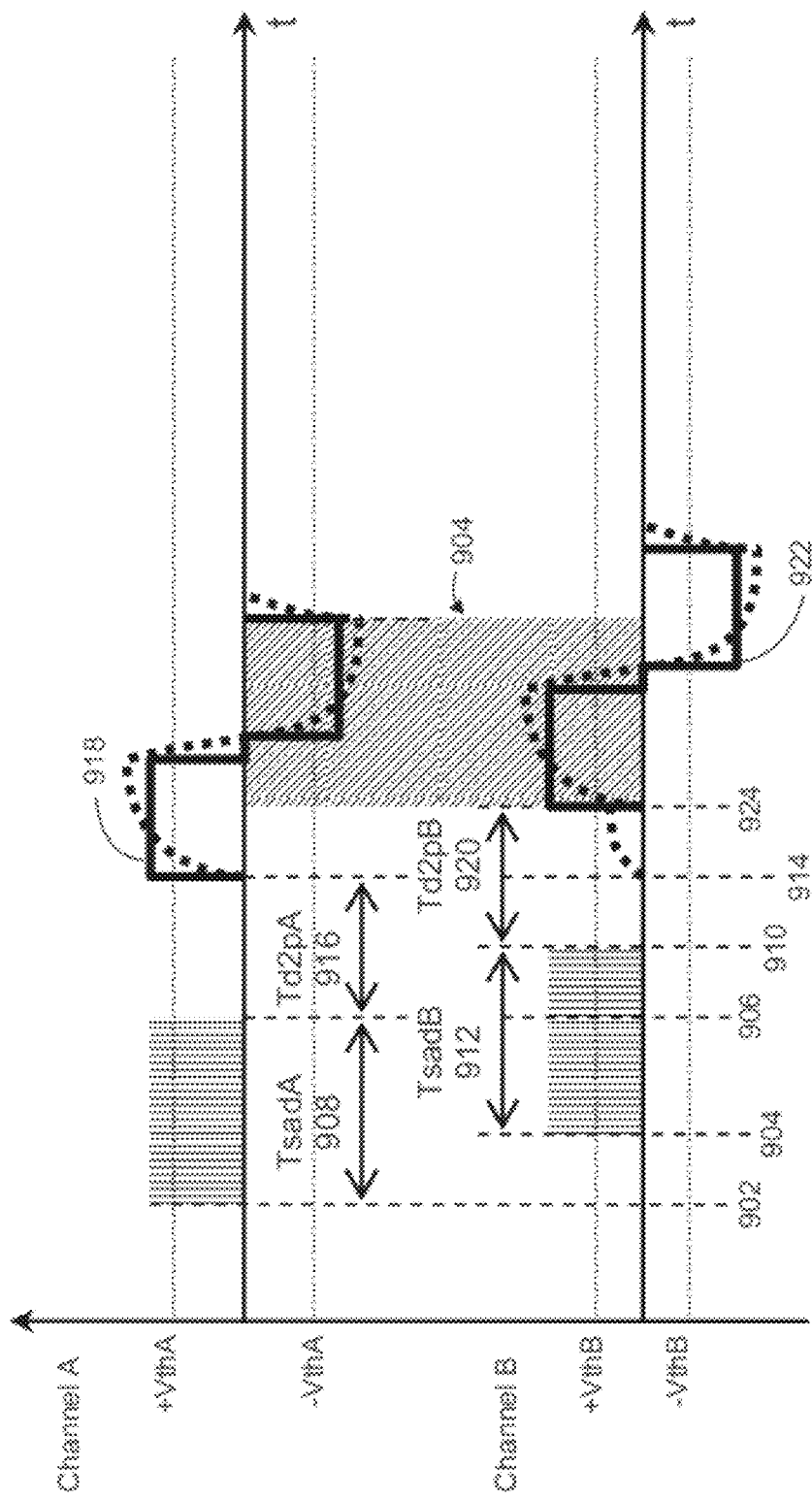
FIG. 9 depicts interfering stimulation waveforms that may be generated by a system implementing the technique of FIG. 7.
Figure 10:
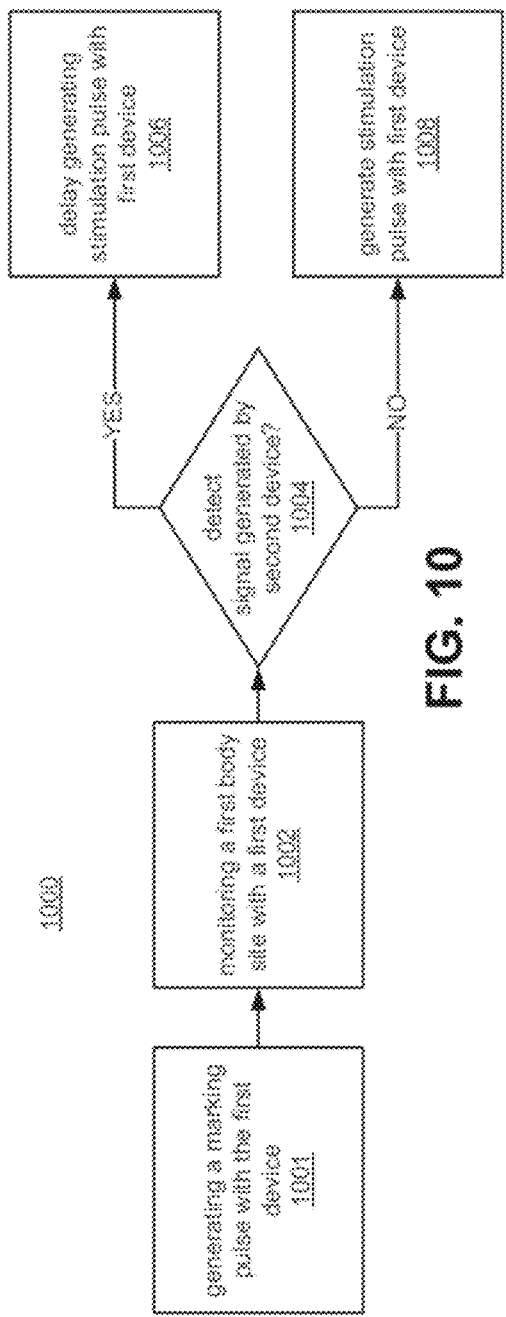
FIG. 10 is a flow diagram of a stimulation interference avoidance technique.

In certain implementations, the stimulation avoidance system is configured to not only monitor other stimulation signals and delay providing stimulation pulses when other signals are detector, but is also configured to provide marking pulses and another auxiliary functionality to address interferences that may be caused by system-based delays between the time at which a stimulation module determines that a stimulation pulse may be generated and the time at which generation of that pulse actually begins. Such delays are in part due to the finite speed at which information can travel within a device (e.g., between processing circuitry and pulse generating circuitry), as well as other physical limitations. A consequence of such delays is illustrated in FIG. 9 and exemplary solutions are illustrated by FIG. 10. For a Channel X, the delay time between the time at which a stimulation module determines that a stimulation pulse may be generated and the time at which generation of that pulse actually begins will be denoted as $Td2p$ (recognizing that this delay time may be different for different channels). $Td2p$ may be minimized, for example, by choosing appropriate circuit components and architectures.

In FIG. 9, at the time 902, stimulation module A begins monitoring a first body site by measuring a voltage (e.g., at a skin surface site) over a stimulation activity detection period 908 of duration TsadA on Channel A 102 (in accordance with the step 702 of FIG. 7). At the time 904, stimulation module B begins monitoring a voltage (e.g., at a different skin surface site) over a stimulation activity detection period 912 of duration TsadB on Channel B 104 (in accordance with the step 702 of FIG. 7). At the time 906, since no activity was detected by the stimulation module A during the stimulation activity detection period 908, the stimulation module A determines to generate a stimulation pulse on Channel A 102 (in accordance with the step 704 of FIG. 7). At the time 910, since no activity was detected by the stimulation module B during the stimulation activity detection period 912, the stimulation module B determines to generate a stimulation pulse on Channel B 104 (in accordance with the step 704 of FIG. 7). At the time 914, after a delay period 916 of duration $Td2pA$ from Channel A's decision time 906, stimulation module A begins generating a stimulation pulse 918 on Channel A 102 (in accordance with the step 706 of the flow diagram 700 of FIG. 7). At the later time 924, after a delay period 920 of duration $Td2pB$ from Channel B's decision time 910, stimulation module B begins generating a stimulation pulse 922 on Channel B 104 (in accordance with the step 706 of the flow diagram 700 of FIG. 7). The stimulation pulses 918 and 922 interfere, as indicated by the shaded region 904. In FIG. 9, the pulses from two different stimulation channels are offset in time by a period less than the time $Td2p$ of one channel (i.e., the delay time between the decision to generate a pulse and the generation of that pulse), which allows additional stimulation interference to occur. While faster electronic components may enable a decrease in the duration of $Td2p$, most devices exhibit a non-zero decision-to-pulse delay period $Td2p$.

The interference avoidance systems and methods disclosed herein include a number of variations and examples that address non-zero delay periods by accounting for such latency. (In certain applications, the stimulation interference arising from the non-zero delay period $Td2p$ is ignored as negligible, particularly when the interference is imperceptible to a user.)

In one example, a marking pulse is used, as illustrated by the flow diagram 1000 of FIG. 10 (in addition to or instead of the process depicted by the flow diagram 700 of FIG. 7). At the step 1001, a first device generates a first marking pulse. A second device may also generate a second marking pulse. In some implementations, the marking pulse is generated by the first device prior to or in concert with beginning a stimulation activity detection period as described above. A marking pulse is a very short pulse (e.g., approximately 25 μs) that cannot be strongly perceived by the user but is detected by the second device coupled to the user when the first and second devices share an energy transmissive pathway through the user's body. For example, the second device may be configured to detect marking pulses generated by the first device when interference between stimulation pulses generated by the first and second devices may be perceptible to the user. In other words, when the first and second devices have significant probability of causing interference perceptible to the user (e.g., the two devices are not spaced apart by a substantial distance, or are not operating at different or non-multiple frequencies), the second device may detect the marking pulses generated by the first device. In response to detecting a marking pulse, the second device delays providing a stimulation signal to avoid interfering with the stimulation signal to be generated by the first device.

After generating the marking pulse, the first device performs the remainder of the process illustrated by the flow diagram 1000 as described above for the flow diagram 700 of FIG. 7. In particular, steps 1002, 1004, 1006 and 1008 are performed by the first device (e.g., a stimulation module) in accordance with any of the examples described above for the steps 702, 704, 706 and 708, respectively, of FIG. 7. The monitoring in step 1004 extends over a stimulation activity detection period of a duration Tsad. In certain applications, different channels have different durations Tsad of their stimulation activity detection periods. In some applications, for a stimulation Channel X, TsadX is greater than $Td2pX$ (where the latter is the minimum delay time between the decision to generate a pulse and the actual generation of that pulse, as described above with reference to FIG. 9).

Figure 11:
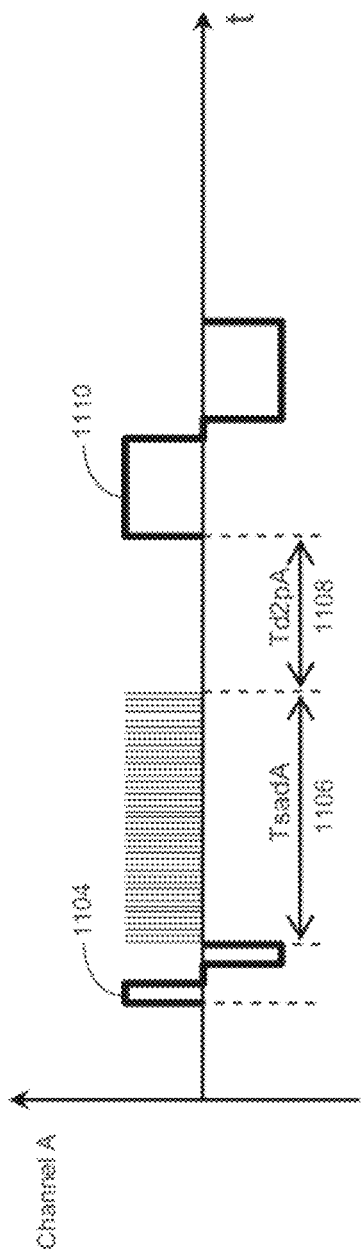
FIG. 11 is an illustration of a waveform that may be generated by a system implementing the technique of FIG. 10.

FIG. 11 depicts an illustrative waveform that may be produced by Channel A 102 in accordance with an implementation of the flow diagram 1000 of FIG. 10. The waveform includes a marking pulse 1104, a channel-specific stimulation activity detection period 1106 of duration TsadA, a decision-to-pulse delay period 1108 of duration $Td2pA$ and a stimulation pulse 1110. As illustrated, the marking pulse 1104 is a very short pulse (e.g., approximately 25 μs) that cannot be strongly perceived by the user, if perceived at all.

Figure 12A:
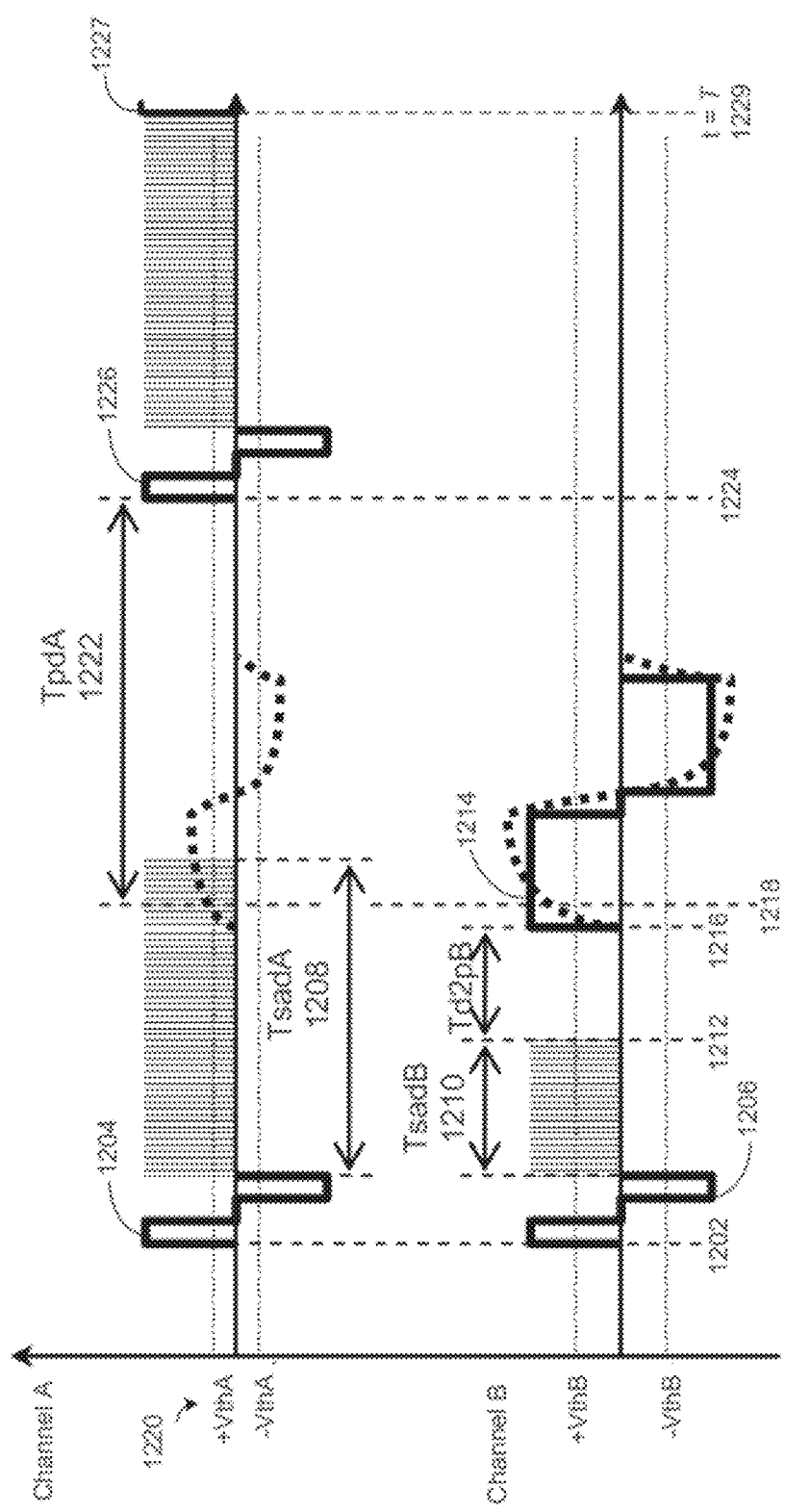
FIGS. 12A-12B depict waveforms that may be generated by a system implementing the technique of FIG. 10.
Figure 12B:
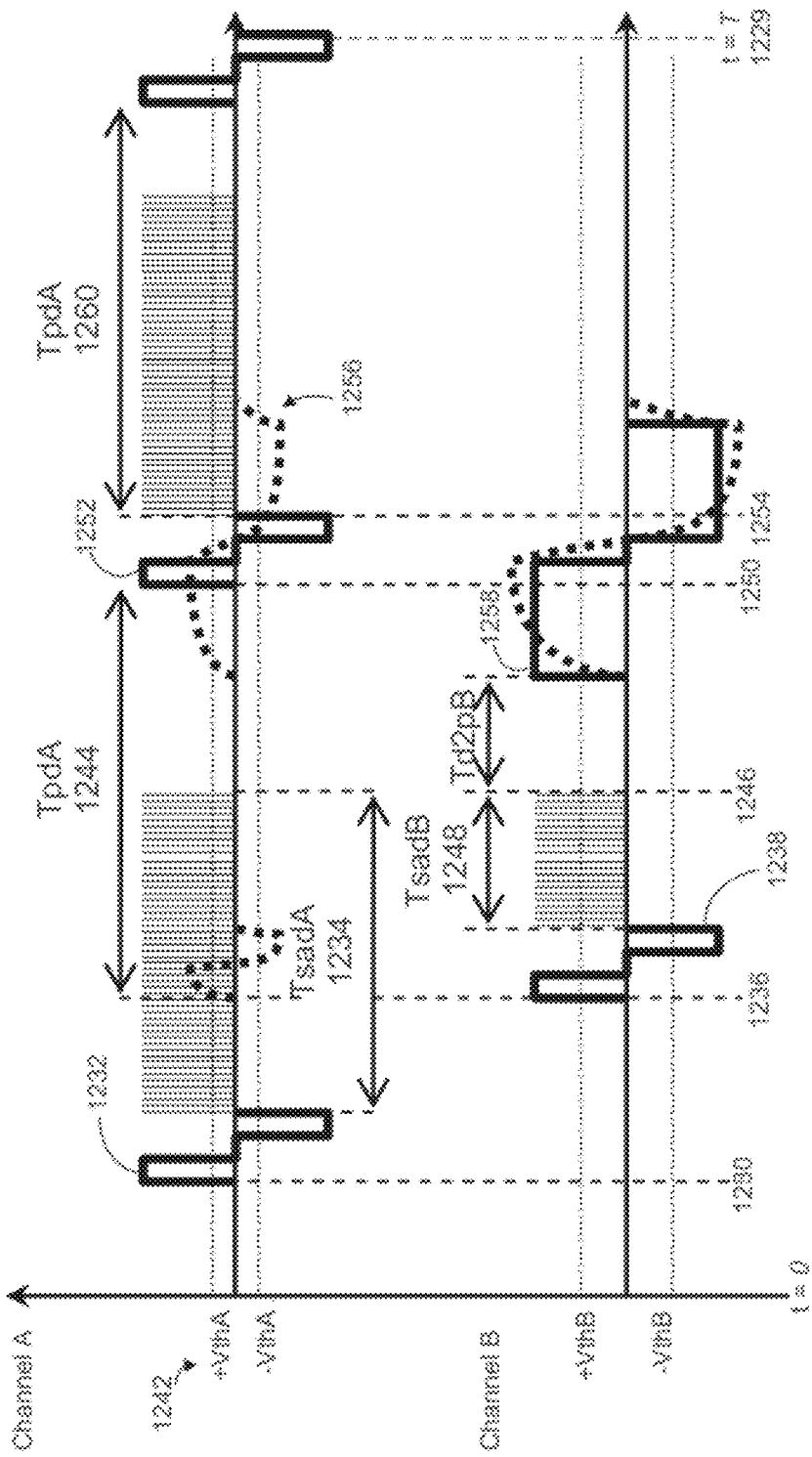

FIGS. 12A-12B depict two examples of waveforms produced by two devices in a stimulation interference avoidance system over a period of duration T, each executing the steps of the flow diagram 1000 of FIG. 10. In FIG. 12A, at the time 1202, Channels A 102 and B 104 generate marking pulses 1204 and 1206, respectively (the step 1001 of FIG. 10). After generating the marking pulses 1204 and 1206, each of Channels A 102 and B 104 begins its stimulation activity detection period (the periods 1208 and 1210, respectively) to detect stimulation signals coming from neighboring electrodes or other stimulation sources along or under the user's skin. The duration of this period is TsadA for Channel A 102, and TsadB for Channel B 104. As shown, the system is pre-programmed so that TsadA is longer than TsadB, with TsadB starting at the same time as TsadA but ending before TsadA ends. Thus, at the time 1212, Channel B 104 has completed its stimulation activity detection period without detecting any significant stimulation and therefore prepares to generate a stimulation pulse. At the time 1216, after a delay of Td2pB from its decision time 1212, Channel B 104 then generates a stimulation pulse 1214. At the time 1218, Channel A 102 detects significant stimulation from another source (here, stimulation from Channel B that exceeds +VthA 1220) and thus commences its retry delay period 1222 of duration TpdA. At the time 1224, Channel A 102 has completed its retry delay period 1222, whereupon it generates a marking pulse 1226 and again executes the step 1001 of FIG. 10. At the time 1229, Channel A 102 detects no competing signal from another source and therefore provides the stimulation pulse 1227 (only partially shown in FIG. 12A). In this manner, Channel A 102 does not fire during the firing of Channel B 104, thus avoiding interference.

In FIG. 12B, at the time 1230, Channel A 102 generates a marking pulse 1232 and then begins its stimulation activity detection period 1234. At the time 1236, Channel B 104 generates a marking pulse 1238. Also approximately at the time 1236 (or a short time after), Channel A 102 detects a signal outside the negligible range (here, the range [−VthA,+VthA]). This signal arises from the marking pulse 1238 from Channel B 104, and thus Channel A 102 commences its retry delay period 1244 of duration TpdA. After generating its marking pulse 1238, Channel B 104 begins its stimulation activity detection period 1248 of duration TsadB. As shown, Channel B 104 has completed its stimulation activity detection period 1248 without registering any significant signal, and Channel B 104 proceeds to generate a stimulation pulse 1258. At the time 1250, Channel A 102 has completed its retry delay period 1244 and generates another marking pulse 1252. At the time 1254, Channel A 102 detects a voltage signal 1256 outside the range [−VthA,+VthA], and thus begins another retry delay period 1260 of duration TpdA.

The marking pulse generated at the step 1001 of FIG. 10 may take any of a variety of shapes, including one or more square pulses, one or more sine pulses, one or more triangle pulses, or any combination of shapes of pulses. In certain applications, the marking pulse generated at the step 1001 has frequency components similar to those in the stimulation pulses intended to be generated. Due to the complex impedances encountered by an energy signal as it moves through a user's body, similarity in frequency content between the marking pulse and the stimulation pulse may improve the performance of the stimulation avoidance techniques described herein by distributing the energy of the marking pulse over energy pathways in the same way that the energy of the stimulation pulse is distributed. For example, a muscle-building treatment protocol in an electrostimulation system may include 50 Hz electrical stimulation (e.g., delivered as a sequence of 8-second pulses) during a contraction phase and 4 Hz electrical stimulation (e.g., delivered as a sequence of 8-second pulses) during a relaxation phase. In this scenario, marking pulses delivered during the contraction phase may include 50 Hz electrical stimulation (or have a substantial 50 Hz frequency component, or a substantial frequency component that is an integer multiple of 50 Hz, or any combination thereof), and marking pulses delivered during the relaxation phase may include 4 Hz electrical stimulation (or have a substantial 4 Hz frequency component, or a substantial frequency component that is an integer multiple of 4 Hz, or any combination thereof).

The parameters of a marking pulse may be dynamically adjusted and personalized according to the tissue characteristics of the user, the spacing of the stimulation modules, and the stimulation treatments to be applied. In certain implementations, a marking pulse set-up process is automatically performed before the start of a stimulation treatment session. During this set-up process, a stimulation module generates a sequence of trial marking pulses with different parameters (e.g., increasing amplitudes, increasing pulse widths, different wave shapes, etc.). When a user perceives one of the trial marking pulses (e.g., by experiencing a pain, a twitch, or another physical sensation), the user activates an input on the stimulation module or a management module. The user input indicates that the particular trial marking pulse generated prior to the user input was perceptible to the user, and thus the parameters of that particular trial marking pulse should not be used for the marking pulses to be generated at the step 1001. In implementations in which a sequence of trial marking pulses is generated with increasing amplitude during the set-up process, the stimulation module may respond to user input of perceptibility by setting the amplitude of future marking pulses to the amplitude of the last trial marking pulse not perceptible to the user.

A marking pulse may be encoded with information regarding a stimulation module that generated the marking pulse, a characteristic of the stimulation treatment to be delivered via the marking pulse channel, or any other information regarding the source of the marking pulse. In such implementations, a first device that receives an indication of the marking pulse (e.g., at the step 1006 of FIG. 10) may decode the marking pulse to determine information about the stimulation channel that generated the marking pulse. The first device may use this information to adjust the treatment delivered by its associated stimulation module. For example, a marking pulse may have information about the schedule of stimulation treatment to be applied on its associated channel; upon receiving an indication of the marking pulse and decoding its information, the first device may adjust its stimulation schedule so that its firing is offset compared to the stimulation schedule of the second device, thereby reducing the likelihood of interference with stimulation pulses generated at the marking pulse channel. In certain applications, the first device stores the decoded marking signal information in a memory, and transmits the information to another device (such as the management module 202 of FIG. 2). The encoding/decoding of information within marking pulses may be performed according to any known technique, including amplitude, frequency and phase modulation, pulse width modulation, pulse code modulation, encoded data strings appended to the beginning or end of a marking pulse, spread spectrum techniques, and any combination thereof.

In certain implementations, the systems are programmed to prioritize the firing of one or more channels of stimulation with respect to each other, in which cases the marking pulse from a particular channel may have features indicative of information regarding the channel's priority level. The systems may apply a priority level or ranking during detected interference periods to prioritize which channel may fire next. A marking pulse that indicates priority may include specific frequencies, amplitudes, and pulse shapes. The marking pulse can thus be said to be encoded with the priority information. In some such implementations, a priority level is established based on a particular type of stimulation treatment delivered by a channel. For example, a pain-blocking stimulation treatment may be programmed to have a first/higher priority than a conflicting muscle-exercising stimulation treatment, and so should be applied first and ahead of the exercising treatment. In other implementations, a channel's priority level is determined based on the probability that the stimulation device will fail to meet adequate stimulation treatment goals if the channel is delayed when delivering its next stimulation pulse. For example, a stimulation module that has been deferred from generating its stimulation pulse for a certain number of cycles (e.g., by repeatedly reaching the step 708 when operating according to the flow diagram 700 of FIG. 7) is increasingly likely to provide insufficient stimulation treatment as such pulses are missed. In certain implementations, the likelihood of failure for an overall stimulation protocol is determined based on the deviation between the actual stimulation frequency from its pre-programmed frequency. When the deviation exceeds a threshold (e.g., an absolute threshold or a threshold relative to a desired frequency, such as 5%), the marking pulse generated by the channel at the step 1001 (FIG. 10) includes an encoded priority level identifier indicating that the stimulation module is at risk for failing to provide its scheduled treatment and should be given priority in generating its next stimulation pulse. A stimulation module receiving this signal decodes the priority level, compares the decoded priority level to its own priority level (as stored in memory) and delays its next stimulation pulse if the decoded priority level is higher than its own priority level. In some implementations, a stimulation module receiving a signal at the step 1002 detects the presence of a "priority" indicator in the received signal and delays its next stimulation pulse (without performing a comparison of priority levels). Identification of a priority level may be implemented in software (e.g., via pattern recognition or decision algorithms implemented by a special- or general-purpose processing device), in hardware (e.g., analog or digital logic circuitry), or a combination of hardware and software.

Any of the priority information encoding techniques disclosed herein may be applied to stimulation pulses instead of or in addition to marking pulses. Different encoding methods may be used for stimulation pulses than marking pulses, and different encoding methods may be used for pulses generated by different channels. A particular encoding method may be chosen to be compatible with the stimulation treatment applied (and not introduce unsafe levels or types of stimulation to the user).

As indicated above, exemplary systems may include an internal stimulation clock (e.g., the stimulation clock 237 of the stimulation module 204 of FIG. 2) to drive stimulation pulse firing. To reduce the impact of inherent shifts in the frequency of any clock circuit, a phenomenon known as "drift," the stimulation system may include further processors to prevent excessive drift of the stimulation clocks included in each stimulation module using the systems and methods disclosed below.

Figure 13:
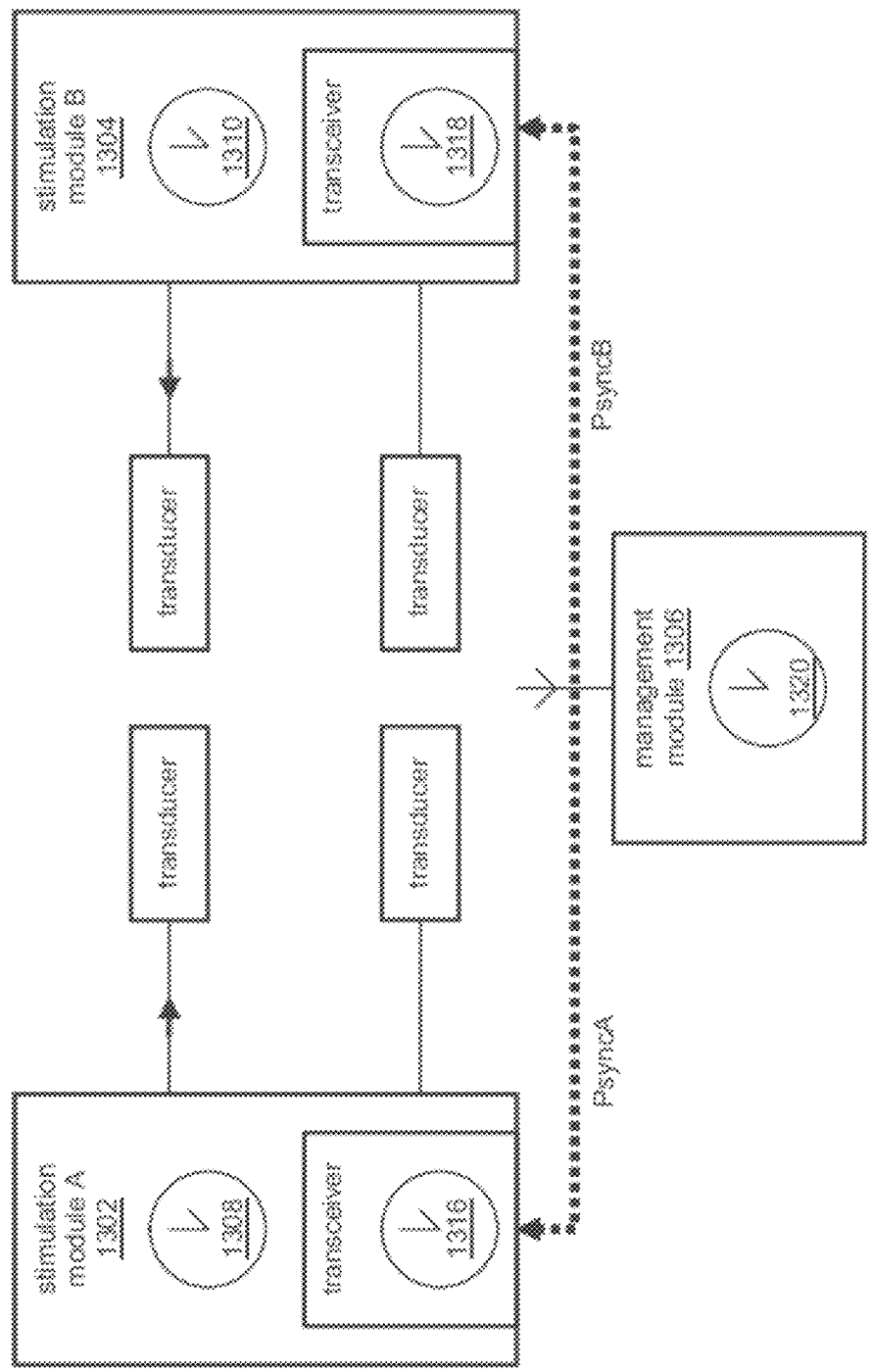
FIG. 13 is a diagram of a two-channel stimulation system with clock synchronization.

FIG. 13 depicts an implementation of a stimulation system in which the stimulation module A 1302 and the stimulation module B 1304 are in wireless communication with a management module 1306 (e.g., as described above for the system 200 of FIG. 2), with each of the stimulation modules A 1302 and B 1304 including a stimulation clock (the clocks 1308 and 1310, respectively) for timing stimulation pulses. Each of the stimulation modules A 1302 and B 1304 includes a transceiver for conducting wireless communication with the management module 1306 according to a wireless communication protocol coordinated, in part, by the communication clocks 1316 and 1318, respectively. The management module 1306 also includes a communication clock 1320. The stimulation clocks 1308 and 1310 are synchronized according to the following exemplary stimulation clock synchronization technique. The exemplary technique is illustrated with a two-module system for ease of illustration, but is applicable to systems with more than two modules and/or channels and may be implemented alone or with any of the stimulation interference avoidance systems and methods described herein.

In the system of FIG. 13, the management module 1306 communicates wirelessly with stimulation modules A 1302 and B 1304 using a wireless transceiver configured to operate at a given communications frequency (e.g., 2.4 GHz). Periodically, the communication clocks 1316 and 1318 included in the stimulation modules are wirelessly synchronized with the communication clock 1320 in the management module 1306 in order to maintain successful wireless communication (according to known techniques). For example, 2.4 GHz wireless communication requires communication clocks synchronized to within about 30 parts per million. However, the separate stimulation clocks 1308 and 1310 included in the stimulation modules A 1302 and B 1304, respectively, have their own specific accuracy and are subject to drift with respect to each other, as discussed above.

To address that drift, the management module 1306 generates communication clock synchronization signals PsyncA and PsyncB periodically (e.g., once every 1 ms), which are received by the transceivers included in each of the stimulation modules A 1302 and B 1304 and used to synchronize their communication clocks 1316 and 1318, respectively. The stimulation modules A 1302 and B 1304 use these communication synchronization signals to synchronize the stimulation clocks 1308 and 1310 that govern pulse generation to reduce drift. Stimulation clock synchronizations may not need to be performed prior to each stimulation pulse. Instead, stimulation clock synchronizations may be performed at intervals of duration Treg which depend on the drift of the stimulation clocks included in the stimulation modules A 1302 and B 1304.

Figure 14:
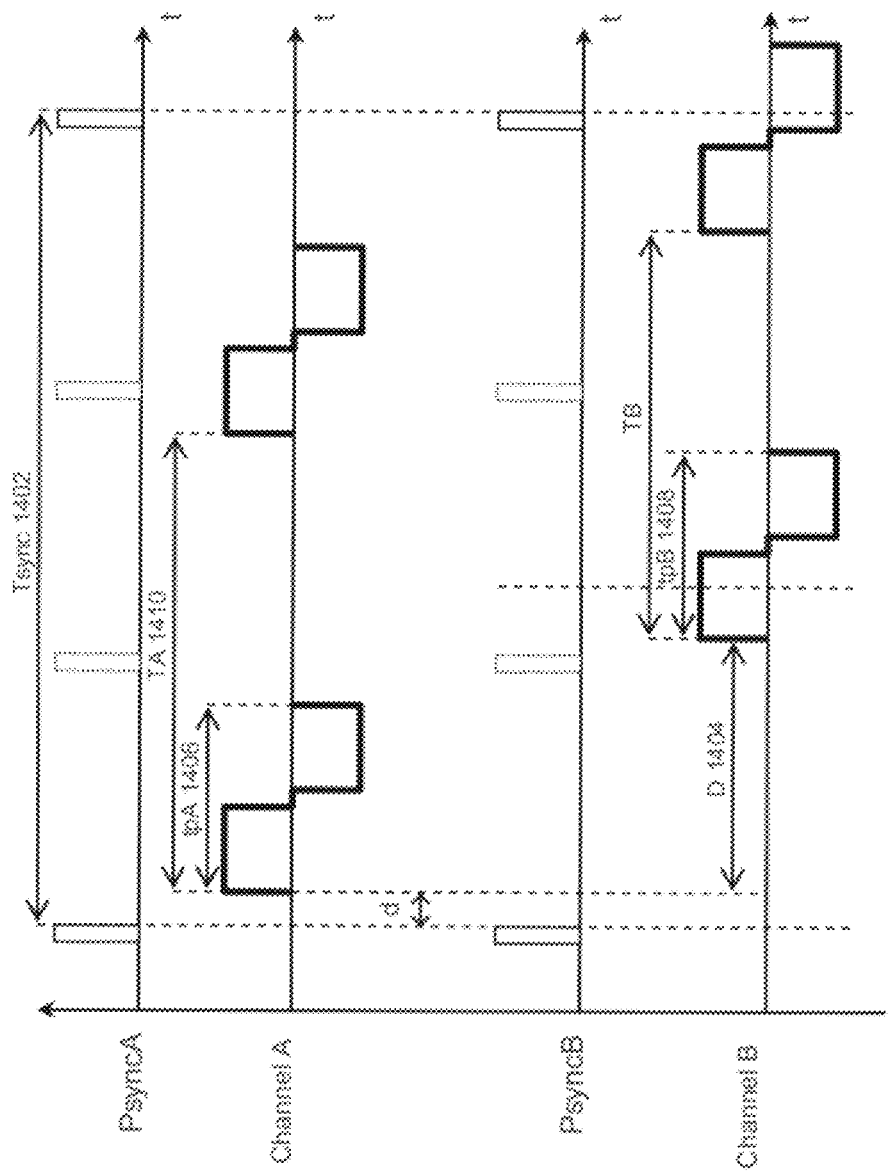
FIG. 14 depicts waveforms that may be generated according to a stimulation interference avoidance technique using the clock synchronization system of FIG. 13.

In the discussion below, the following notation is used and illustrated with reference to FIG. 14. Any of the following quantities may be calculated, stored in a memory, communicated from another device and/or received from an operator input, and updated as necessary. The stimulation modules A 1302 and B 1304 have a reaction delay period d (FIG. 14) between a synchronization signal and the stimulation module response. The reaction delay period d may be approximately the same for multiple stimulation modules, or may be different. The stimulation module A 1302 generates pulses of maximum duration TpAmax (e.g., TpA 1406 of FIG. 14) with a minimum period of repetition of TAmin (e.g., TA 1410 of FIG. 14). The stimulation clock 1308 of the stimulation module A 1302 operates with a period of TckA. Analogously, the stimulation module B 1304 generates pulses of maximum duration TpBmax (e.g., TpB 1408 of FIG. 14) according to the stimulation clock 1310 which operates with a period of TckB. The drift between the stimulation clocks 1308 and 1310 of the stimulation modules A 1302 and B 1304 can be evaluated according to the expression $$\text{Drift} = |TckA - TckB|/TckA, \quad (1)$$

which represents the factor by which the period of the stimulation clock A 1308 advances on the period of the stimulation clock B 1310, for every cycle of the stimulation clock A 1308.

A stimulation pulse generated by the stimulation module B 1304 will avoid interference with the stimulation pulses generated by the stimulation module A 1302 if the B pulse falls entirely within the period between two consecutive A pulses. This can be achieved by delaying the start of the B pulse from the start of the A pulse by a time interval given by $$D = TpA\max + (TA\min - TpA\max - TpB\max)/n \quad (2)$$

where n>1 is a parameter that allows the delay between the beginning of the A pulse and the beginning of the B pulse to be tuned between a maximum value D=TAmin−TpBmax (when n=1) and a minimum value D=TpAmax (as n→∞). For example, when n=2, the pulse generated by the stimulation module B 1304 is equally spaced in time between two consecutive pulses generated by the stimulation module A 1302.

To prevent or reduce overlap between stimulation pulses generated by the stimulation modules A 1302 and B 1304, the drift between the stimulation clocks A 1308 and B 1310 is kept below the time gap between the completion of a stimulation pulse from the stimulation module A 1302 and the start of a stimulation pulse from the stimulation module B 1304. The amount of time between stimulation clock synchronizations, denoted by Tsync (e.g., Tsync 1402 of FIG. 14), may be computed by determining how long it will take for the drift between stimulation clocks to "close the gap" between stimulation pulses from the stimulation modules A 1302 and B 1304. In certain applications, stimulation systems adjust the stimulation clocks to perform synchronizations at an intervals calculated by $$T\text{sync} = (D - TpA\max)/\text{Drift}. \quad (3)$$

A numerical example of the operation of this system is illustrative. For example, assume that the stimulation clocks A 1308 and B 1310 each drift within 30 parts per million (ppm) of their same nominal (i.e., pre-programmed or preselected) periods TpAmax=TpA=TpBmax=TpB. In this example, the maximal separation between the two stimulation clocks occurs when each stimulation clock drifts in an opposite direction, resulting in 60 ppm of drift that may contribute to stimulation interference and should be corrected. When the stimulation pulses generated by transducers of the stimulation modules A 1302 and B 1304 are each composed of a 400 μs positive current pulse, a 70 μs zero current period, and a 70 μs negative current period, then TpAmax=TpA=TpBmax=TpB=1000 μs=1 ms. When the frequency of stimulation generated by the stimulation module A 1302 is 150 Hz, then TAmin=TA=1/150 Hz=6.67 ms. In certain embodiments, then, the systems and methods disclosed above adjust the stimulation clocks to synchronize the stimulation clocks at intervals calculated using the expressions of Eqs. (2) and (3):

$$D = 1 \text{ ms} + (6.67 \text{ ms} - 1 \text{ ms} - 1 \text{ ms})/2 = 3.335 \text{ ms, and} \quad (4)$$

$$T\text{sync} = (3.335 \text{ ms} - 1 \text{ ms})/0.06 \text{ ms/s} = 30.58 \text{ s} \quad (5)$$

These stimulation systems may synchronize the stimulation clocks approximately every 30.6 s (or more often) to avoid stimulation interference caused by the drift between the stimulation clocks in the stimulation modules A 1302 and B 1304. For example, if the management module 1306 transmits communication clock PSync pulses every 1 ms, a stimulation clock synchronization may be performed at intervals of every 30 Psync pulses.

Any of the stimulation interference avoidance systems and methods described herein may include visual or audio indicators to signal the state of the performance of the stimulation interference avoidance components and/or indicate the occurrence of any stimulation interference avoidance events. The stimulation system 200 of FIG. 2 may use interference avoidance indicators (e.g., displays, LEDs, spoken indicators, tones, electronic messages, writes to electronic memory) via any of the operator interface subsystem 228 of the stimulation module 204, the operator interface subsystem 212 of the management module 202, the computer 208, the remote data source 210, or any other system component. For example, displays, audio outputs or electronic outputs may indicate any one or more of:

a conflict for one or more stimulation modules (e.g., as discussed with reference to the step 706 of FIG. 7);

a deviation between the stimulation treatment delivered by a stimulation module and the stimulation treatment actually delivered; and the occurrence of a stimulation clock synchronization.

It is to be understood that while various illustrative embodiments have been described, the forgoing description is merely illustrative and does not limit the scope of the invention. While several examples have been provided in the present disclosure, it should be understood that the disclosed systems, components, and methods may be embodied in many other specific forms without departing from the scope of the present disclosure.

The examples disclosed can be implemented in sub-combinations with one or more other features described herein. A variety of systems and methods may be implemented based on the disclosure and still fall within the scope of the invention. For example, the systems and methods may be applied to electrical, acoustic, thermal, optical or other energy-based therapy or prophylactic sources. Also, the various features described or illustrated above may be combined or integrated in other systems or certain features may be omitted, or not implemented.

Examples of changes, substitutions, and alterations are ascertainable by one skilled in the art and could be made without departing from the scope of the information disclosed herein. Certain particular aspects, advantages, and modifications are within the scope of the following claims. All references cited herein are incorporated by reference in their entirety and made part of this application.

What is claimed is:

1. A method for reducing interference between a first stimulation program comprising a succession of stimulation pulses generated by a first transducer of a first device applied at a first body site and a second stimulation program comprising a succession of stimulation pulses generated by a second transducer of a second device applied at a second body site, the method comprising:

monitoring the first body site using the first transducer during a first detection period for a signal indicative of a stimulation pulse of the second stimulation program generated by the second transducer;

when a signal indicative of a stimulation pulse of the second stimulation program generated by the second transducer is detected at the first body site using the first transducer during the first detection period, delaying for a first delay period the generation of a stimulation pulse of the first stimulation program by the first transducer, and at the end of the first delay period, generating a stimulation pulse of the first stimulation program using the first transducer; and when a signal indicative of a stimulation pulse of the second stimulation program generated by the second transducer is not detected at the first body site using the first transducer during the first detection period, generating a stimulation pulse of the first stimulation program using the first transducer.

2. The method of claim 1, wherein monitoring the first body site is performed at pre-determined time intervals.

3. The method of claim 1, wherein the first detection period comprises a first pre-determined time period.

4. The method of claim 1, wherein the first delay period comprises a time period with a first random duration.

5. The method of claim 4, wherein the first random duration is selected from between a lower duration limit and an upper duration limit.

6. The method of claim 1, wherein a signal indicative of a stimulation pulse generated with the second transducer comprises a signal having an intensity exceeding a threshold.

7. The method of claim 1, further comprising incrementing a retry counter in response to the delaying.

8. The method of claim 7, further comprising triggering an electronic indicator when the retry counter reaches a retry limit.

9. The method of claim 1, further comprising generating a marking pulse with the first transducer prior to monitoring the first body site during the first detection period.

10. The method of claim 9, wherein the marking pulse signifies a priority level of the first stimulation program to be delivered by the first transducer.

11. The method of claim 1, further comprising:
detecting a marking pulse during the first detection period at the first body site by the first transducer; and
identifying a priority level of the second stimulation program to be delivered by the second transducer in response to detecting the signal indicative of the marking pulse generated by the second transducer.

12. The method of claim 11, delaying for a first delay period the generation of a stimulation pulse of the first stimulation program by the first transducer, wherein the duration of the first delay period is based at least in part on the identified priority level of the second stimulation program to be delivered by the second transducer.

13. The method of claim 1, further comprising:
monitoring the second body site during a second detection period using the second transducer, and
when a signal is detected by the second transducer indicative of a stimulation pulse of the first stimulation program generated by the first transducer, registering a positive body site contact condition for the second transducer.

14. The method of claim 13, wherein registering a positive body site contact condition for the second transducer occurs prior to generating a stimulation pulse with the second transducer.

15. The method of claim 1, further comprising:
monitoring the second body site, using the second transducer, for a second detection period;
when, during the second detection period, a signal is detected by the second transducer indicative of a marking pulse or a stimulation pulse generated by the first transducer, delaying for a second delay period before generating a stimulation pulse with the second transducer; and
when, during the second detection period, a signal is not detected indicative of a marking pulse or a stimulation pulse generated by the first transducer, generating a second stimulation pulse with the second transducer.

16. The method of claim 15, wherein monitoring the first body site is performed at first pre-determined time intervals and monitoring the second body site is performed at second pre-determined time intervals.

17. The method of claim 15, wherein the second delay period is different from the first delay period.

18. The method of claim 15, further comprising:
generating a marking pulse with the first transducer prior to monitoring the first body site using the first transducer for the first detection period; and
generating a marking pulse with the second transducer prior to monitoring the second body site using the second transducer for the second detection period.

19. The method of claim 15, wherein one or more additional transducers are configured to be applied at respectively one or more additional body sites, the method further comprising
monitoring the one or more additional body sites for a detection period; and
during the detection period,
when a signal is detected indicative of a marking pulse or a stimulation pulse generated by at least one of the first and second transducers, delaying for a delay period before generating a stimulation pulse with at least one of the one or more additional transducers, and
otherwise, generating a stimulation pulse with at least one of the one or more additional transducers.

20. The method of claim 1, wherein first and second stimulation clocks are operatively coupled to the first and second transducers, respectfully, the method further comprising:
wirelessly receiving a communication synchronization signal; and,
in response to receiving the communication synchronization signal, adjusting at least one of the first and second stimulation clocks to synchronize the first and second stimulation clocks.

21. The method of claim 20, wherein the step of adjusting a stimulation clock is performed repeatedly, and wherein a plurality of communication synchronization signals are received between successive stimulation clock adjustments.

22. The method of claim 21, wherein the number of communication synchronization signals received between successive stimulation clock adjustments is based at least in part on a frequency of stimulation pulses generated by the first transducer.

23. A method for delivering a first stimulation program with a first electrostimulation device that reduces interference with at least one additional stimulation program delivered by at least one additional electrostimulation device, each stimulation program comprising a succession of stimulation pulses, a first transducer of the first electrostimulation device applied at a first body site, and at least one additional transducer of the at least one additional electrostimulation device applied to at least one additional body site separate from the first body site, the method comprising:
prior to generating a stimulation pulse with the first transducer, monitoring the first body site with the first transducer during a first detection period for a signal indicative of a stimulation pulse generated by the additional transducer of the additional electrostimulation device;

when a signal indicative of a stimulation pulse is detected by the first transducer during the first detection period,
   initiating a delay period for the first transducer that postpones the first transducer from generating a stimulation pulse;
   upon completion of the delay period, monitoring the first body site with the first transducer during an additional detection period for a signal indicative of a stimulation pulse generated by the additional transducer of the additional electrostimulation device; and
   repeating said initiating a delay period and said monitoring the first body site with the first transducer during the additional detection period until a signal indicative of a stimulation pulse generated by the additional transducer of the additional electrostimulation device is not detected during the additional detection period or a retry limit of a retry counter is reached; and when a signal indicative of a stimulation pulse generated by the additional transducer of the additional electrostimulation device is not detected during the first detection period or an additional detection period, generating the stimulation pulse with the first transducer.

24. The method of claim 23, wherein a duration of the delay period for the first transducer is determined based at least in part on characteristics of the signal indicative of a stimulation pulse is detected by the first transducer.

25. The method of claim 23, wherein a duration of the delay period for the first transducer is different than a duration of a delay period for the additional transducer of the additional electro stimulation device.

26. The method of claim 23, wherein, said repeating further comprises:
   incrementing the retry counter; and
   stopping said repeating when the retry limit of the retry counter is reached.

27. The method of claim 26, wherein the retry limit is determined at least in part based on a therapeutically-acceptable variation of the first stimulation program.

28. The method of claim 23, wherein, when a signal indicative of a stimulation pulse is detected by the first transducer during the first detection period, said initiating a delay period for the first transducer occurs upon completion of the first detection.

29. The method of claim 28, wherein, when more than one signal indicative of a stimulation pulse is detected by the first transducer during the first detection period, a duration of the delay period for the first transducer is increased.

* * * * *